United States Patent
Leung et al.

(10) Patent No.: US 6,599,310 B2
(45) Date of Patent: Jul. 29, 2003

(54) SUTURE METHOD

(75) Inventors: Jeffrey C. Leung, Raleigh, NC (US); Matthew A. Megaro, Chapel Hill, NC (US); Gregory Ruff, Chapel Hill, NC (US); Andrew Kaplan, Hillsborough, NC (US)

(73) Assignee: Quill Medical, Inc., Research Triangle Park, NC (US)

( * ) Notice: Subject to any disclaimer, the term of this patent is extended or adjusted under 35 U.S.C. 154(b) by 197 days.

(21) Appl. No.: 09/896,455

(22) Filed: Jun. 29, 2001

(65) Prior Publication Data

US 2003/0014077 A1 Jan. 16, 2003

(51) Int. Cl.⁷ .................................. A61B 17/04
(52) U.S. Cl. ....................... 606/228; 606/232
(58) Field of Search ................ 606/228, 221, 606/222, 223, 224, 225, 213, 215, 216, 229, 230, 231, 232, 144, 148, 149; 128/898

(56) References Cited

U.S. PATENT DOCUMENTS

| | | |
|---|---|---|
| 709,392 A | 9/1902 | Brown |
| 733,723 A | 7/1903 | Lukens et al. |
| 789,401 A | 5/1905 | Acheson |
| 816,026 A | 3/1906 | Meier |
| 1,142,510 A | 6/1915 | Engle |
| 1,321,011 A | 11/1919 | Cottes |
| 1,728,316 A | 9/1929 | Wachenfeldt |
| 1,886,721 A | 11/1932 | O'Brien |
| 2,201,610 A | 5/1940 | Dawson, Jr. |
| 2,232,142 A | 2/1941 | Schumann |
| 2,254,620 A | 9/1941 | Miller |
| 2,421,193 A | 5/1947 | Gardner |
| 2,472,009 A | 5/1949 | Gardner |
| 2,684,070 A | 7/1954 | Kelsey |
| 2,779,083 A | 1/1957 | Eaton |
| 2,817,339 A | 12/1957 | Sullivan |
| 2,910,067 A | 10/1959 | White |

(List continued on next page.)

FOREIGN PATENT DOCUMENTS

| | | |
|---|---|---|
| DE | 4302895 A | 8/1994 |
| EP | 1075843 A1 | 2/2001 |
| WO | WO 00/51658 | 9/2000 |

OTHER PUBLICATIONS

"Drilled End Surgical Needles", B.G. Sulzle, Inc., Syracuse, New York, Jul. 2002.

(List continued on next page.)

*Primary Examiner*—A. Vanatta
(74) *Attorney, Agent, or Firm*—Moore & Van Allen PLLC; Michael G. Johnston

(57) ABSTRACT

A method is provided for joining and holding closed a wound in bodily tissue using a barbed suture including sharp pointed ends. The pointed end of the suture is inserted on a first side of the wound and pushed through the faces of the wound to an exit point on the second side of the wound that is longitudinally spaced in a first direction from the insertion point in the first side of the wound. The first end of the suture is pulled out of the tissue for drawing the first portion of the suture through the tissue while bringing the two sides of the wound together to a closed position along the first portion of the suture in the tissue. The second pointed end of the suture is inserted into the tissue at one side of the wound and pushed through the faces of the wound to an exit point on the other side of the wound longitudinally spaced in a second direction from the point of insertion of the second end of the suture at the one side of the wound. The second end is pulled out of the tissue for drawing the second portion of the suture through the tissue while bringing the sides of the wound together to the closed position along the second portion of the suture in the tissue.

27 Claims, 19 Drawing Sheets

U.S. PATENT DOCUMENTS

| | | | |
|---|---|---|---|
| 2,988,028 A | 6/1961 | Alcamo | |
| 3,068,869 A | 12/1962 | Shelden et al. | 128/337 |
| 3,068,870 A | 12/1962 | Levin | 128/337 |
| 3,123,077 A | 3/1964 | Alcamo | 128/335.5 |
| 3,166,072 A | 1/1965 | Sullivan, Jr. | 128/334 |
| 3,209,754 A | 10/1965 | Brown | 128/337 |
| 3,214,810 A | 11/1965 | Mathison | 24/87 |
| 3,221,746 A | 12/1965 | Noble | 128/334 |
| 3,234,636 A | 2/1966 | Brown | 29/212 |
| 3,273,562 A | 9/1966 | Brown | 128/337 |
| 3,352,191 A | 11/1967 | Crawford | 85/14 |
| 3,378,010 A | 4/1968 | Codling et al. | 128/325 |
| 3,385,299 A | 5/1968 | Le Roy | 128/337 |
| 3,494,006 A | 2/1970 | Brumlik | 24/204 |
| 3,525,340 A | 8/1970 | Gilbert | 128/337 |
| 3,527,223 A | 9/1970 | Shein | 128/329 |
| 3,586,002 A | 6/1971 | Wood | 128/337 |
| 3,608,095 A | 9/1971 | Barry | 3/1 |
| 3,608,539 A | 9/1971 | Miller | 128/2 |
| 3,683,926 A | 8/1972 | Suzuki | 128/334 R |
| 3,716,058 A | 2/1973 | Tanner, Jr. | 128/337 |
| 3,825,010 A | 7/1974 | McDonald | 128/337 |
| 3,981,307 A | 9/1976 | Borysko | |
| 4,069,825 A * | 1/1978 | Akiyama | 606/158 |
| 4,073,298 A | 2/1978 | Le Roy | 128/337 |
| 4,259,959 A | 4/1981 | Walker | 128/337 |
| 4,317,451 A | 3/1982 | Cerwin et al. | 128/325 |
| 4,428,376 A | 1/1984 | Mericle | 128/335 |
| 4,430,998 A | 2/1984 | Harvey et al. | 128/335 |
| 4,434,796 A | 3/1984 | Karapetian et al. | 128/335 |
| 4,454,875 A | 6/1984 | Pratt et al. | 128/92 B |
| 4,467,805 A | 8/1984 | Fukuda | 128/334 C |
| 4,505,274 A | 3/1985 | Speelman | 128/337 |
| 4,510,934 A | 4/1985 | Batra | 128/335.5 |
| 4,531,522 A | 7/1985 | Bedi et al. | 128/335 |
| 4,548,202 A | 10/1985 | Duncan | 128/334 C |
| 4,610,251 A | 9/1986 | Kumar | 128/334 R |
| 4,635,637 A | 1/1987 | Schreiber | 128/337 |
| 4,637,380 A | 1/1987 | Orejola | 128/334 C |
| 4,653,486 A | 3/1987 | Coker | 128/92 YF |
| 4,669,473 A | 6/1987 | Richards et al. | 128/334 C |
| 4,676,245 A | 6/1987 | Fukuda | 128/334 C |
| 4,719,917 A | 1/1988 | Barrows et al. | 128/334 R |
| 4,776,337 A | 10/1988 | Palmaz | 606/108 |
| 4,841,960 A | 6/1989 | Garner | 128/92 YF |
| 4,873,976 A | 10/1989 | Schreiber | 128/334 R |
| 4,887,601 A | 12/1989 | Richards | 606/219 |
| 4,976,715 A | 12/1990 | Bays et al. | 606/77 |
| 4,994,073 A | 2/1991 | Green | 606/220 |
| 4,997,439 A | 3/1991 | Chen | 606/216 |
| 5,002,562 A | 3/1991 | Oberlander | 606/221 |
| 5,007,921 A | 4/1991 | Brown | 606/221 |
| 5,026,390 A | 6/1991 | Brown | 606/221 |
| 5,047,047 A | 9/1991 | Yoon | 606/216 |
| 5,053,047 A | 10/1991 | Yoon | 606/223 |
| 5,084,063 A | 1/1992 | Korthoff | |
| 5,102,418 A | 4/1992 | Granger et al. | |
| 5,123,911 A | 6/1992 | Granger et al. | |
| 5,123,913 A | 6/1992 | Wilk et al. | 606/232 |
| 5,192,302 A | 3/1993 | Kensey et al. | 606/213 |
| 5,207,694 A | 5/1993 | Broome | 606/148 |
| 5,222,976 A | 6/1993 | Yoon | 606/223 |
| 5,246,441 A | 9/1993 | Ross et al. | 606/53 |
| 5,258,013 A | 11/1993 | Granger et al. | |
| 5,269,783 A | 12/1993 | Sander | 606/72 |
| 5,292,326 A | 3/1994 | Green et al. | 606/143 |
| 5,320,629 A | 6/1994 | Noda et al. | 606/139 |
| 5,342,376 A | 8/1994 | Ruff | 606/151 |
| 5,425,746 A | 6/1995 | Proto et al. | 606/224 |
| 5,425,747 A | 6/1995 | Brotz | 606/228 |
| 5,450,860 A | 9/1995 | O'Connor | 128/898 |
| 5,500,991 A | 3/1996 | Demarest et al. | |
| 5,533,982 A | 7/1996 | Rizk et al. | |
| 5,546,957 A | 8/1996 | Heske | 128/754 |
| 5,584,859 A | 12/1996 | Brotz | 606/228 |
| 5,683,417 A * | 11/1997 | Cooper | 606/223 |
| 5,702,462 A | 12/1997 | Oberlander | |
| 5,716,376 A | 2/1998 | Roby et al. | |
| 5,722,991 A | 3/1998 | Colligan | |
| 5,931,855 A | 8/1999 | Buncke | 606/228 |
| 5,984,933 A * | 11/1999 | Yoon | 606/232 |
| 6,012,216 A | 1/2000 | Esteves et al. | |
| 6,056,778 A | 5/2000 | Grafton et al. | 623/20 |
| 6,083,244 A * | 7/2000 | Lubbers et al. | 606/232 |
| 6,163,948 A | 12/2000 | Esteves et al. | |
| 6,241,747 B1 | 6/2001 | Ruff | 606/216 |
| 6,270,517 B1 * | 8/2001 | Brotz | 606/228 |

OTHER PUBLICATIONS

"Up Lifting (Aptos Threads)", http://www.ccpr.com.br/upl–l.htm, Aug. 19, 2002, pp. 1–2.

Sulamanidze et al., "Facial Lifting with "Aptos" Threads", http://www.fonendo.com, Jul. 18, 2001, pp. 1–4.

McKenzie, "An Experimental Multiple Barbed Suture for the Long Flexor Tendons of the Palm and Fingers", *The Journal of Bone and Joint Surgery*, vol. 49B, No. 3, Aug. 1967, pp. 440–447.

* cited by examiner

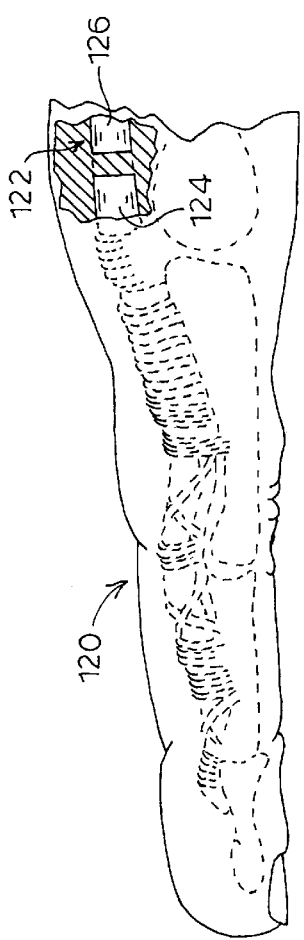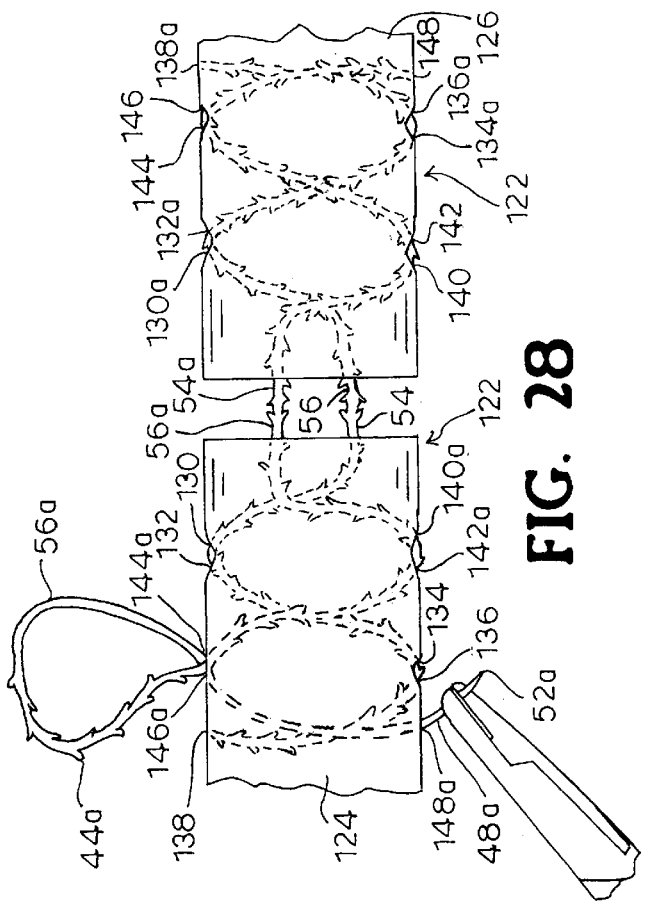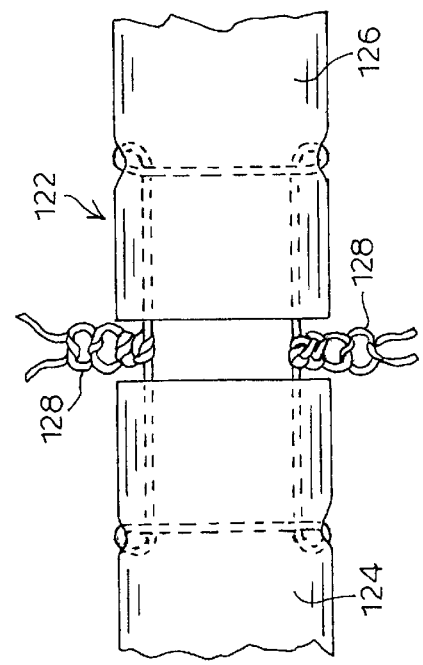

SUTURE METHOD

BACKGROUND

This invention relates generally to a method for joining bodily tissue in surgical applications and wound repair, and more particularly to a surgical suturing method for joining bodily tissue using a suture having a plurality of barbs which permit the suture to be pulled through the tissue in one direction but resisting movement of the suture relative to the tissue in the opposite direction.

Surgical or accidental wounds are typically closed with a length of filament introduced into the tissue by a sharp metal needle attached to one end of the filament. This device is known as a "suture". Sutures are used to make "stitches" to close the wound for holding tissues together for healing and regrowth. Sutures are used in surgical procedures for wound closure, to close the skin in plastic surgery, to secure damaged or severed tendons, muscles or other internal tissues, and in microsurgery on nerves and blood vessels. Generally, the suture needle is caused to penetrate and pass through the tissue pulling the suture through the tissue. The opposing faces of the tissue are then moved together, the needle is removed, and the ends of the suture are tied in a knot. The suture forms a loop as the knot is tied. The knotting procedure allows the tension on the filament to be adjusted to accommodate the particular tissue being sutured and control of approximation, occlusion, attachment or other conditions of the tissue. The ability to control tension is extremely important regardless of the type of surgical procedure being performed.

Suturing is a time-consuming part of most surgical procedures, particularly in microsurgery and endoscopic surgery where there is insufficient space to properly manipulate the suture. Loop sutures can leave scars where they penetrate skin. For adequate closure of some wounds, the suture material must be of a high tensile strength and thus a large diameter thereby increasing scarring. The loop suture also constricts blood flow to the tissue it surrounds, promoting necrosis of the wound margins which compromises healing and increases infection risks. Further, the tissue is distorted as it is secured by the suture loop due to excess tension on the knots. Localized tensions from the knots are the culprit for scar formation. The bulk of the knots are also an impediment to wound healing in internal applications.

Alternatives to conventional sutures for wound closure are known, including fasteners such as staples, clips, tacks, clamps and the like. The fasteners are usually positioned transversely across a wound for joining or approximating each side of adjacent tissue layers laterally. Fasteners have relatively high strength and save time, but are not as accurate as sutures and are bulky and may be painful to remove. Fasteners are also generally unsuitable for deeper layers of tissue. Moreover, fasteners do not provide the advantage of adjustable tension obtained by the knotting of a length of suture material.

Surface adhesive tapes and glues are often used on skin to hold small wounds closed to permit healing. However, these products have relatively low tensile strength and are not useful in many situations.

Other techniques proposed include electrical coagulation and lasers. However, no acceptable alternative has been found which offers the advantages of suturing and tying in most surgical procedures.

One possible alternative is a barbed suture. A barbed suture includes an elongated body having one or more spaced barbs projecting from the surface of the body along the length of the body. The barbs are configured to allow passage of the suture in one direction through tissue but resist movement of the suture relative to the tissue in the opposite direction. In wound closure, a barbed suture is passed through tissue at each of the opposed sides of a wound. The wound is closed by pushing the sides of the wound together with the barbs maintaining the sutures in place and resisting movement of the tissue away from this position. The advantage of using barbed sutures is the ability to put tension in the tissue with less slippage of the suture in the wound. The barbed suture spreads out the holding forces evenly thereby significantly reducing tissue distortion. Since knots do not have to be tied, there is a time saving and the elimination of suture knots improves cosmetic effects and promotes wound healing. Barbed sutures also allow better apposition of tissue since the incised or insulted tissues are brought together and secured with almost no movement immediately. Unlike the conventional suturing method wherein tension is applied by pulling on the end of the suture after placement, barbed sutures permit tissue to be approximated and held snug during suturing. This is especially advantageous in closing long incisions. The result is better healing when the tissue levels are harmoniously matched as the cosmetic effect is more pronounced at skin level. Moreover, if there is an accidental breakage of the barbed suture, the wound is minimally disturbed. With conventional sutures, dehiscence would occur.

Despite the advantages offered by barbed sutures, the tensile strength of a barbed suture is less than a loop suture of equivalent size. This is due to the reduced tensile strength resulting from imparting the barb structure onto the body of the suture, which reduces its effective diameter. This limitation is not significant since larger barbed sutures with greater tensile strength can be utilized. However, the conventional methods for introducing barbed sutures into tissue still do not exhibit the same biomechanical performance of looped sutures.

For the foregoing reasons there is a need for a suturing method for joining tissue in surgical applications and wound repair which is efficient and expedites the surgical procedure. Ideally, the new method allows a surgeon to suture in an efficient manner to quickly the approximate tissue with appropriate tension. The new method should preserve blood flow, improve wound healing strength, prevent distortion of the tissue and minimize scarring. The method should also incorporate the self-retaining benefits of the barbed suture with the holding power of conventional suturing methods. A particularly useful method would be utilized in surgical applications where space is limited such as microsurgery, endoscopic or arthroscopic surgery.

SUMMARY

It is therefore an object of the present invention to provide a method for joining and holding the sides of wounds or surgical incisions in contact or apposition for healing or regrowth.

Another object of the present invention is to provide a method of suturing having characteristics similar to conventional suturing methods such that a surgeon can use techniques similar to those used for suturing with a needle and a length of suture material.

A further object of the present invention is to provide a method of suturing using a barbed suture.

Still another object of the present invention is to provide a method of suturing useful in endoscopic and arthroscopic procedures and microsurgery.

Still further, an object of the present invention is to provide a method of suturing which minimizes scarring and provides a strong retention force between the joined tissues.

Yet another object of the present invention is to provide an efficient procedure for closing wounds, incisions and severed tissues such as tendons, joint capsules, ligaments, bones, vascular structures, valves, and hollow organs.

According to the present invention there is provided a method for joining and holding closed a wound in bodily tissue to allow tissue healing and regrowth together of the two sides of the wound or reconfiguration in vivo using a barbed suture including sharp pointed ends for penetrating the tissue. The method comprises the steps of inserting the first pointed end of the suture into the tissue at a first side of the wound and pushing the first end of the suture through the tissue until the first end of the suture extends out of the tissue at an exit point in the face of the wound below the surface of the tissue at the first side of the wound. The first end of the suture is pulled out of the tissue for drawing the first portion of the suture through the tissue leaving a length of the first portion of the suture in the tissue between the point of insertion in the first side of the wound and the exit point in the face of the wound at the first side of the wound. The first end is then inserted into the face of the tissue below the surface of the tissue at a second side of the wound and pushed through the tissue until the first end of the suture extends out of the tissue at an exit point on the second side of the wound longitudinally spaced in a first direction from the insertion point in the first side of the wound. The first end of the suture is pulled out of the tissue for drawing the first portion of the suture through the tissue while bringing the two sides of the wound together to a closed position along the first portion of the suture in the tissue and leaving a length of the first portion of the suture in the tissue between the point of insertion in the first side of the wound and the exit point in the second side of the wound. Next, the second pointed end of the suture is inserted into the tissue at one side of the wound and pushed through the tissue until the second end of the suture extends out of the tissue at an exit point in the face of the tissue below the surface of the tissue at the one side of the wound. The second end is pulled out of the tissue for drawing the second portion of the suture through the tissue and leaving a length of the second portion of the suture in the tissue between the point of insertion in the one side of the wound and the exit point in the face of the wound at the one side of the wound. The second end of the suture is inserted into the face of the tissue below the surface of the tissue at the other side of the wound and pushed through the tissue until the second end of the suture extends out of the tissue at an exit point on the other side of the wound longitudinally spaced in a second direction from the point of insertion of the second end of the suture at the one side of the wound. The second end is pulled out of the tissue for drawing the second portion of the suture through the tissue while bringing the sides of the wound together to the closed position along the second portion of the suture in the tissue and leaving a length of the second portion of the suture in the tissue between the point of insertion in the one side of the wound and the exit point in the other side of the wound.

Also according to the present invention there is provided a method for joining and holding closed a wound in bodily tissue to allow tissue healing and regrowth together of the two sides of the wound or reconfiguration in vivo using a barbed suture including sharp pointed ends for penetrating the tissue. The method comprises the steps of inserting a first pointed end of the suture into the tissue at a point laterally spaced from one side of the wound, pushing the suture through the tissue to extend out of the tissue in a first face of the wound and penetrating an opposite second face of the open wound until the point of the suture emerges from the tissue at an exit point laterally spaced from the other side of the wound and longitudinally spaced in a first direction from the point of insertion of the first end of the suture at the one side of the wound. The suture is gripped at the point end and pulled out of the tissue for drawing a first portion of the suture having barbs for resisting movement in the opposite direction through the tissue leaving a length of the first portion of the suture body in the tissue of the wound. The second pointed end of the suture is inserted into the tissue at the point of insertion of the first end at the one side of the wound. The second end is pushed through the tissue to extend out of the tissue at a point in the first face of the wound and penetrating the opposite face of the open wound until the point of the second end emerges from the tissue at an exit point laterally spaced from the other side wound and longitudinally spaced in a second direction from the point of insertion of the second end of the suture at the one side of the wound. The second end of the suture is gripped at the point end and pulled out of the tissue for drawing a second portion of the suture including barbs for resisting movement in the opposite direction through the tissue leaving a length of the second portion of the suture body in the tissue of the open wound.

Further according to the present invention a method is provided for joining and holding closed a wound in tissue using a barbed suture including curved pointed ends. A pointed end is inserted into the tissue below the surface at a first face of the wound and pushed along a curvilinear path until the point of the first end of the suture extends from the tissue at an exit point in the first face of the wound longitudinally spaced in a first direction from the insertion point in the first face of the wound. The first end of the suture is gripped at the point end and pulled out of the tissue for drawing the first portion of the suture including barbs for resisting movement in the opposite direction through the tissue leaving a length of the first portion of the body of the suture in the tissue of the open wound. The first end of the suture is next inserted at a point in the second face of the wound, pushed through the tissue along a curvilinear path until the point end of the suture extends from the tissue at an exit point in the second face of the wound longitudinally spaced in the first direction from the insertion point in the second face of the wound and reinserted in the first face. The previous steps are repeated for advancing longitudinally along the wound in the first direction to one end of the wound. The second pointed end of the suture is then inserted into the tissue at the second face of the wound adjacent the initial point of insertion of the first end of the suture in the first face of the wound and pushed through the tissue along a curvilinear path until the point of the second end extends from the tissue at an exit point in the second face of the wound longitudinally spaced in a second direction from the point of insertion of the second needle in the second face of the wound. The second end of the suture is gripped at the point end and pulled out of the tissue for drawing the second portion of the suture including barbs for resisting movement in the opposite direction through the tissue leaving a length of the second portion of the body in the tissue of the open wound. The second end is next inserted at a point in the first face of the wound and pushed through the tissue along a curvilinear path until the point end of the needle extends from the tissue at an exit point in the first face of the wound longitudinally spaced in the second direction from the exit point of the second needle in the second face of the wound and reinserted in the second face. The previous steps are repeated for advancing longitudinally along the wound in the second direction to the other end of the wound as necessary depending on the size of the wound to close the wound.

Still further according to the present invention, another method for joining and holding closed an open wound in bodily tissue to allow tissue healing and regrowth together of the two sides of the wound using a barbed suture with curved pointed ends is provided. This method includes the steps of inserting the first pointed end of the suture into the tissue at a first face of the open wound adjacent one end of the wound and pushing the first end of the suture through the tissue along a curvilinear path until the point end extends from the tissue at an exit point in the first face of the wound longitudinally spaced from the one end of the wound in a direction toward the other end of the wound. The first end of the suture is inserted into the second face of the open wound and pushed along a curvilinear path until the point end extends from the tissue at an exit point in the second face of the wound longitudinally spaced from the exit point in the first face of the wound toward the other end of the wound. The first end of the suture is gripped at the point end and pulled out of the tissue for drawing the first portion of the suture including barbs for resisting movement in the opposite direction through the tissue leaving a length of the first portion of the suture body in the tissue of the open wound. The end of the suture is entered in the first face of the wound and the previous steps are repeated for advancing longitudinally along the wound in the direction toward the other end of the wound until the other end of the wound is reached. Next, the second pointed end of the suture is inserted into the tissue at the second face of the open wound adjacent the initial point of insertion of the first end of the suture at the one end of the wound. The second end of the suture is pushed through the tissue along a curvilinear path until the point end extends from the tissue at an exit point in the second face of the wound longitudinally spaced from the one end of the wound in a direction toward the other end of the wound. The second end of the suture is then inserted into the first face of the open wound adjacent the exit point of the first end of the suture and pushed along a curvilinear path until the point end extends from the tissue at an exit point in the first face of the wound longitudinally spaced from the point of insertion in the first face of the wound in a direction toward the other end of the wound. The second end of the suture is then gripped at the point end and pulled out of the tissue for drawing the second portion of the suture including barbs for resisting movement in the opposite direction, through the tissue leaving a length of the second portion of the body in the tissue of the open wound, and reinserted into the second face of the wound. The previous steps are repeated for advancing longitudinally along the wound in the direction toward the other end of the wound until the other end of the wound is reached and the remaining second portion of the suture removed.

Yet further according to the present invention, a method is provided for joining two ends of severed internal tissue to allow healing and regrowth together of the ends of the internal tissue in vivo using a barbed suture including curved pointed ends. The internal tissue repair method comprises the steps of inserting the first pointed end of a first suture into one end of the internal tissue and pushing the end through the internal tissue along a curvilinear path until the point of the suture extends from an exit point in a first side of the internal tissue longitudinally spaced from the one end of the internal tissue. The end of the first suture is then inserted into the first side of the internal tissue adjacent the exit point and pushed along a curvilinear path until the point end extends from an exit point in the second side of the internal tissue longitudinally spaced from the insertion point in the first side of the internal tissue. The first end of the suture is gripped at the point end and pulled out of the internal tissue for drawing the first portion of the suture, including barbs for resisting movement of the suture in the opposite direction, through the internal tissue leaving a length of the first portion of the suture in the internal tissue. The previous steps are repeated for advancing the first portion of the suture longitudinally along the internal tissue in the direction away from the one end. The previous steps at the other end of the severed tissue with the second end of the suture.

The methods of the present invention are useful in wound closure and repair of internal tissue such as muscle, tendons and ligaments. The methods can be used in open and closed surgery, including arthroscopic and endoscopic surgery.

BRIEF DESCRIPTION OF THE DRAWINGS

For a more complete understanding of the present invention, reference should now be had to the embodiments shown in the accompanying drawings and described below. In the drawings:

FIG. 23 is a side elevation view of a finger with a portion of the outer layer of tissue cut-away to schematically show a severed tendon;

FIG. 24 is a plan view of the Kessler method for joining two ends of a severed tendon;

FIGS. 25–28 are perspective views of an embodiment of a method according to the present invention for joining two ends of a severed tendon.

DESCRIPTION

As used herein, the term "wound" means a surgical incision, cut, laceration, severed tissue or accidental wound in human skin or other bodily tissue, or other condition where suturing, stapling, or the use of another tissue connecting device might be required.

As used herein, the term "tissue" includes tissues such as skin, bone, muscle, organs, and other soft tissue such as tendons, ligaments and muscle.

Certain other terminology is used herein for convenience only and is not to be taken as a limitation on the invention. For example, words such as "upper," "lower," "left," "right," "horizontal," "vertical," "upward," and "downward" merely describe the configuration shown in the FIGS. It is understood that the components may be oriented in any direction and the terminology, therefore, should be understood as encompassing such variations unless specified otherwise.

Figure 1:
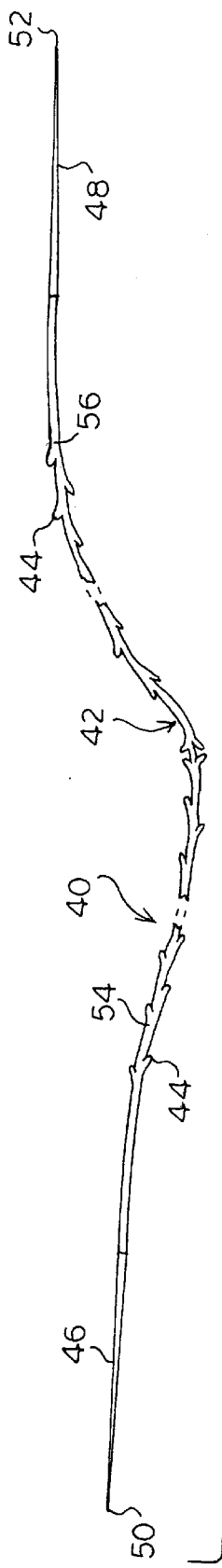
FIG. 1 is a perspective view of an embodiment of a barbed suture with straight pointed ends for use according to the methods of the present invention.
Figure 2:
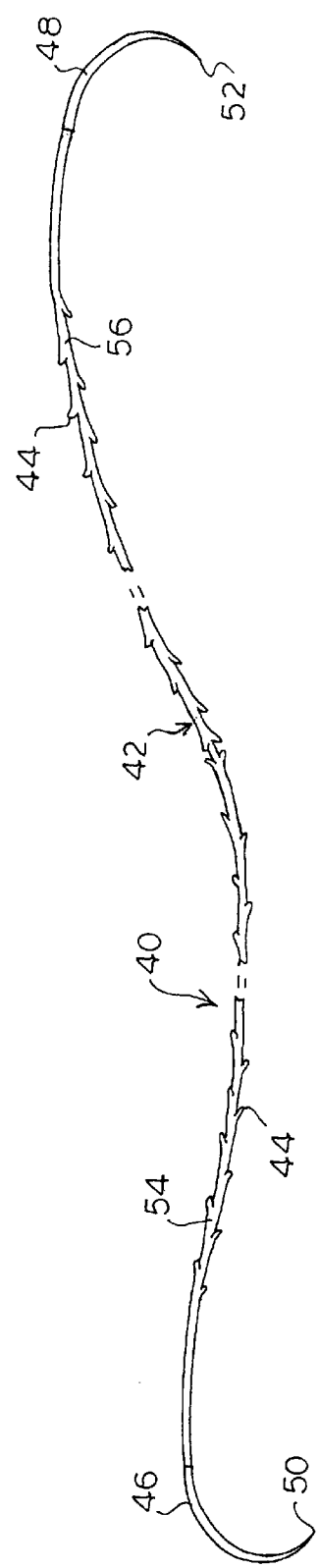
FIG. 2 is a perspective view of a barbed suture with curved pointed ends for use according to the methods of the present invention.

Referring now to the drawings, wherein like reference numerals designate corresponding or similar elements throughout the several views, there is shown in FIGS. 1 and 2 a suture for use according to the present invention and generally designated at 40. The suture 40 includes an elongated body 42 having a plurality of barbs 44 disposed along the length of the body 42. First and second ends 46, 48 of the body 42 terminate in points 50, 52 for penetrating tissue.

The body 42 of the suture 40 is, in one embodiment, circular in cross section. Suitable diameters for the body 42 of the suture 40 range from about 0.001 mm to about 1.0 mm. The body 42 of the suture 40 could also have a non-circular cross-sectional shape which would increase the surface area of the body 42 and facilitate the formation of multiple barbs 44.

The length of the suture 40 can vary depending on several factors such as the extent of the wound to be closed, the type of tissue to be joined, the location of the wound, and the like. A suture 40 of proper length is selected for achieving suitable results in a particular application.

Material for the body 42 of the suture 40 is available in a wide variety of monofilament suture material. The particular suture material chosen depends on the strength and flexibility requirements. In one embodiment, the material for the body 42 is flexible and substantially nonresilient so that the shape of an inserted suture 40 will be determined by the path of insertion and the surrounding tissue. In some applications, however, it may be desirable for at least a portion of the body 42 to have sufficient dimensional stability to assume a substantially rigid configuration during use and sufficient resiliency to return to a predetermined position after deflection therefrom. The portions of the ends 46, 48 of the suture 40 adjacent the points 50, 52 may be formed of a material sufficiently stiff to enable the points 50, 52 to penetrate tissue in which the suture 40 is used when a substantially axial force is applied to the body 42. Variations in surface texture of the body 42 of the suture 40 can impart different interaction characteristics with tissues.

The body 42 can be formed of a bioabsorbable material which allows the suture 40 to be absorbed over time into the tissue as the wound heals. Bioabsorbable material is particularly useful in arthroscopic surgery and methods of suturing. Many compositions useful as bioabsorbable materials can be used to make the body 42 of the suture 40 for use in the methods of the present invention. Generally, bioabsorbable materials are thermoplastic polymers. Selection of the particular material is determined by the desired absorption or degradation time period which depends upon the anticipated healing time for the subject of the procedure. Biodegradable polymers and co-polymers range in degradation time from about one month to over twenty-four months. They include, but are not limited to, polydioxanone, polylactide, polyglycolide, polycaprolactone, and copolymers thereof. Other copolymers with trimethylene carbonate can also be used. Examples are PDS II (polydioxanone), Maxon (copolymer of 67% glycolide and 33% trimethylene carbonate), and Monocryl (copolymer of 75% glycolide and 25% caprolactone). Germicides can also be incorporated into the body 42 of the suture 40 which are retained by the suture 40 to provide long lasting germicidal properties.

The body 42 of the suture 40 can also be formed from non-absorbable material such as nylon, polyethylene terephthalate (polyester), polypropylene, and expanded polytetrafluoroethylene (ePTFE). Alternatively, the suture body 42 can also be formed of metal (e.g. steel), metal alloys, plastic, or the like.

The plurality of barbs 44 is axially-spaced along the body 42 of the suture 40. The barbs 44 are oriented in one direction facing toward the first end 46 of the suture 40 for a first portion 54 of the length of the suture and in an opposite direction facing the second end 48 of the suture 40 for a second portion 56 of the suture. The barbs 44 are yieldable toward the body 42. The barbs 44 on each portion 54, 56 of the suture are oriented so as to allow movement of the suture 40 through the tissue in one direction along with the corresponding end 46, 48 of the suture 40. The barbs 44 are generally rigid in an opposite direction to prevent the suture 40 from moving in the tissue in the opposite direction.

The barbs 44 can be arranged in any suitable pattern, for example, in a helical pattern as shown in FIGS. 1 and 2. The number, configuration, spacing and surface area of the barbs 44 can vary depending upon the tissue in which the suture 40 is used, and depending on the composition and geometry of the suture body. The proportions of the barbs 44 may remain relatively constant while the overall length of the barbs 44 and the spacing of the barbs 44 are determined by the tissue being connected. For example, if the suture 40 is intended to be used to connect the edges of a wound in skin or tendon, the barbs 44 can be made relatively short and more rigid to facilitate entry into this rather firm tissue. If the suture 40 is intended for use in fatty tissue, which is relatively soft, the barbs 44 can be made longer and spaced farther apart to increase the holding ability in the soft tissue. Moreover, the ratio of the number of barbs 44 on the first portion 54 of the suture 40 to the number of barbs 44 on the second portion 56, and the lengths of each portion 54, 56, can vary depending on the application and needs.

The surface area of the barbs 44 can also vary. For example, fuller-tipped barbs 44 can be made of varying sizes designed for specific surgical applications. For joining fat and relatively soft tissues, larger barbs 44 are desired, whereas smaller barbs 44 are more suited for collagen-dense tissues. There are also situations where a combination of large and small barbs 44 within the same structure will be beneficial such as when a suture 40 is used in tissue repair with differing layer structures. Use of the combination of large and small barbs 44 with the same suture 40 wherein barb 44 sizes are customized for each tissue layer will ensure maximum anchoring properties.

The barbs 44 may be formed on the surface of the body 42 according to any suitable method, including cutting, molding, and the like. The preferred method is cutting with acute angular cuts directly into the suture body 42 with cut portions pushed outwardly and separated from the body 42 of the suture 40. The depth of the barbs 44 formed in the suture body 42 depends on the diameter of the suture material and the depth of cut. A particularly suitable device for cutting a plurality of axially spaced barbs 44 on the exterior of suture filaments utilizes a cutting bed, a cutting bed vise, a cutting template, and a blade assembly to perform the cutting. When operated, the cutting device has the ability to produce a plurality of axially spaced barbs 44 in the same or random configuration and at different angles in relation to each other. Various other suitable methods of cutting the barbs 44 have been proposed including the use of a laser. The barbs 44 could also be cut manually. However, manually cutting the barbs 44 is labor intensive, decreases consistency, and is not cost effective. The suture 40 could also be formed by injection molding, extrusion, stamping and the like. The suture 40 can be packaged in any number of desired pre-cut lengths and in pre-shaped curves.

The ends 46, 48 of the suture 40 may be straight (FIG. 1) or curved (FIG. 2). In one embodiment, the ends 46, 48 of the suture 40 may be surgical needles secured at each end of the body 42 of the suture 40 so that the body 42 extends between the shank ends of the two needles. The needles are preferably constructed of stainless steel or other surgical grade metal alloy. The needles may be secured to the suture body 42 by means of adhesives, crimping, swaging, or the like, or the joint may be formed by heat shrinkable tubing. A detachable connection may also be employed such that the needles may be removed from the body 42 of the suture 40 by a sharp tug or pull or by cutting. The length of the needles is selected to serve the type of tissue being repaired so that the needles can be completely removed leaving the suture body 42 in the desired position within the tissue.

Barbed sutures suitable for use according to the methods of the present invention are described in U.S. Pat. No. 5,342,376, entitled "Inserting Device for a Barbed Tissue Connector", U.S. Pat. No. 6,241,747, entitled "Barbed Bodily Tissue Connector", and U.S. Pat. No. 5,931,855. The contents of U.S. Pat. No. 5,342,376, U.S. Pat. No. 6,241,747, and U.S. Pat. No. 5,931,855 are hereby incorporated by reference.

According to the present invention, a surgical procedure using barbed sutures 40 is provided for binding together living tissue for healing and regrowth or reconfiguration in vivo. In general, when the suture 40 is used in tissue to repair a wound, the suture is passed through tissue at each of the sides of the wound. The point 50 at one end 46 of the suture 40 is inserted into a first side of a wound such that the point 50 pierces the tissue and the barbs 44 on the end portion 54 of the suture 40 corresponding to the one end 46 yield toward the body 42 to facilitate movement of the suture 40 through the tissue in the direction of insertion. The other end 48 of the suture 40 is also inserted into a side of the wound and advanced through the tissue in like manner. The sides or faces of the wound are then moved together along the suture portions 54, 56 within the tissue to close the wound. The barbs 44 of the suture 40 grasp the surrounding tissue on each side of the wound and maintains the edges of the wound in position during healing. The leading ends 46, 48 of the suture 40 protruding from the tissue are then cut and discarded. In one embodiment, ends of the suture 40 in the tissue are made to lie below the surface of the skin by first depressing the skin immediately around the ends and severing the suture body 42 closely against the skin. The skin will rise to cover the ends of the suture 40.

FIGS. 3–6 show a section of tissue including a portion of a patient's skin 58 and subcutaneous tissue defining a wound 60 from the surface of the skin 58 down into the tissue. It is understood that the wound 60 in the tissue can be of any configuration and from any anatomical part or organ of the body. Accordingly, depending on the configuration of the wound, the wound may comprise several sides and faces. However, the wounds depicted in the FIGS. are straight incisions in the skin 58 to reduce the complexity of the description of the method of the present invention. It is understood that the applicants do not intend to limit the method of the present invention to the closure of only straight incisions.

In this embodiment of the method of the present invention, the user, such as a surgeon, selects a suture 40 of sufficient length and having straight ends 46, 48. As noted above, in one embodiment, the ends 46, 48 may be surgical needles.

Figure 3:
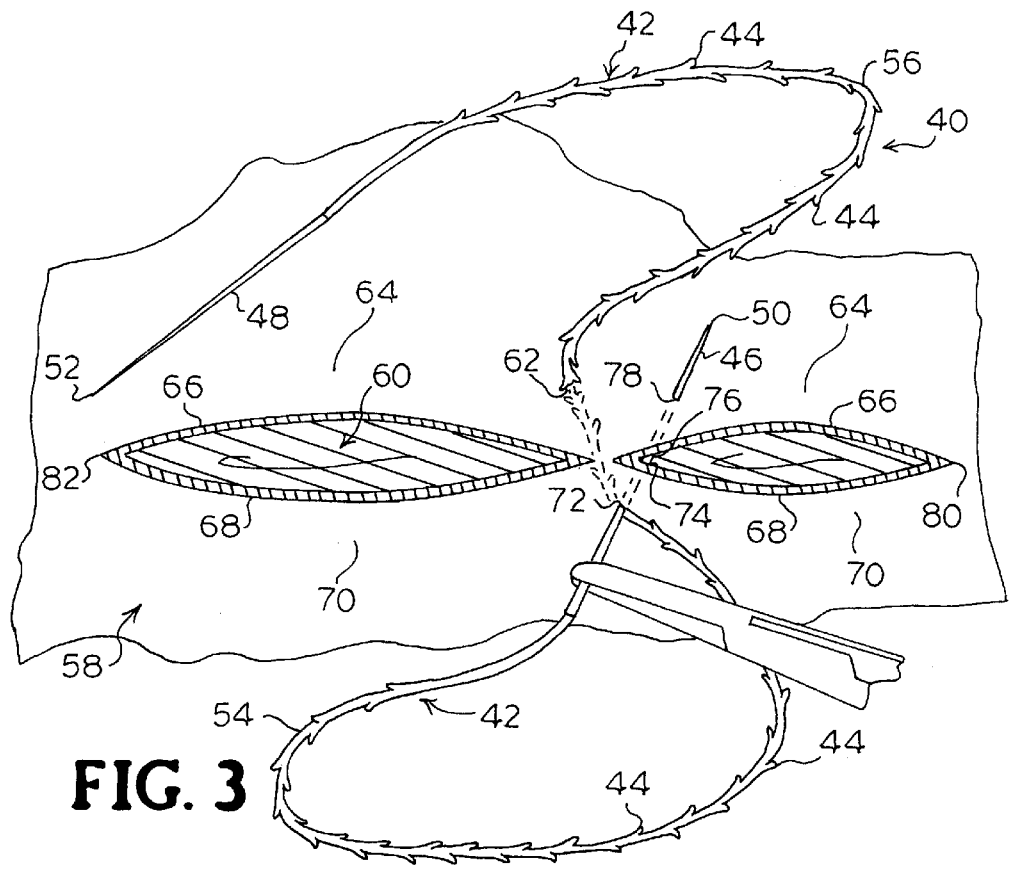
FIGS. 3–6 are plan views of an embodiment of a method according to the present invention for joining two sides of an open wound in tissue.

Referring to FIG. 3, the surgeon inserts the needle 46 at the end of the first portion 54 of the suture 40 into the tissue at a point 62 on a first side 64 of the wound 60 and laterally spaced from the face 66 of the wound 60 at the first side 64. The surgeon advances the needle 46 along a selected substantially straight path through the tissue to extend out of the tissue at a subcutaneous point (not shown) in the first face 66 of the wound 60 and subcutaneously penetrating a point (not shown) in a face 68 of a second side 70 of the wound 60. The surgeon continues to advance the needle 46 through the tissue until the point 50 of the needle emerges from the tissue at a distal end of the selected path at an exit point 72 on the second side 70 of the wound 60. The exit point is laterally spaced from the face 68 of the second side 70 of the wound and longitudinally spaced in a first direction from the point of insertion 62 at the first side 64 of the wound 60. The surgeon grips the exposed portion of the needle 46 and pulls the needle 46 out of the tissue. This action draws the first portion 54 of the suture 40 having barbs 44 for resisting movement in the opposite direction through the tissue until the barbs 44 on the second portion 56 engage the surface of the skin 58 at the insertion point 62 preventing further advancement of the suture 40 through the tissue. A length of the first portion 54 of the suture body 42 is thus positioned in the tissue along the selected path. The faces 66, 68 of the wound 60 are approximated by pushing the adjacent sides 64, 70 of the tissue together along the first portion 54 of the body 42 of the suture 40 in the tissue.

The needle 46 is next inserted into the tissue at the exit point 72 and advanced along a substantially straight path through the tissue to extend out of the tissue at a subcutaneous point 74 in the second face 68 of the wound 60 and subcutaneously penetrating a point 76 in the first face 66 of the wound 60. The surgeon continues to advance the needle 46 through the tissue until the point end 50 emerges from the tissue at a distal end of the selected path at an exit point 78 on the first side 64 of the wound 60 that is laterally spaced from the first face 66 and longitudinally spaced in the first direction from the point of insertion 72 at the second side 70 of the wound 60. Again the surgeon grips the exposed portion of the needle 46 and pulls the needle 46 out of the tissue, drawing the first portion 54 of the suture 40 through the tissue.

Figure 4:
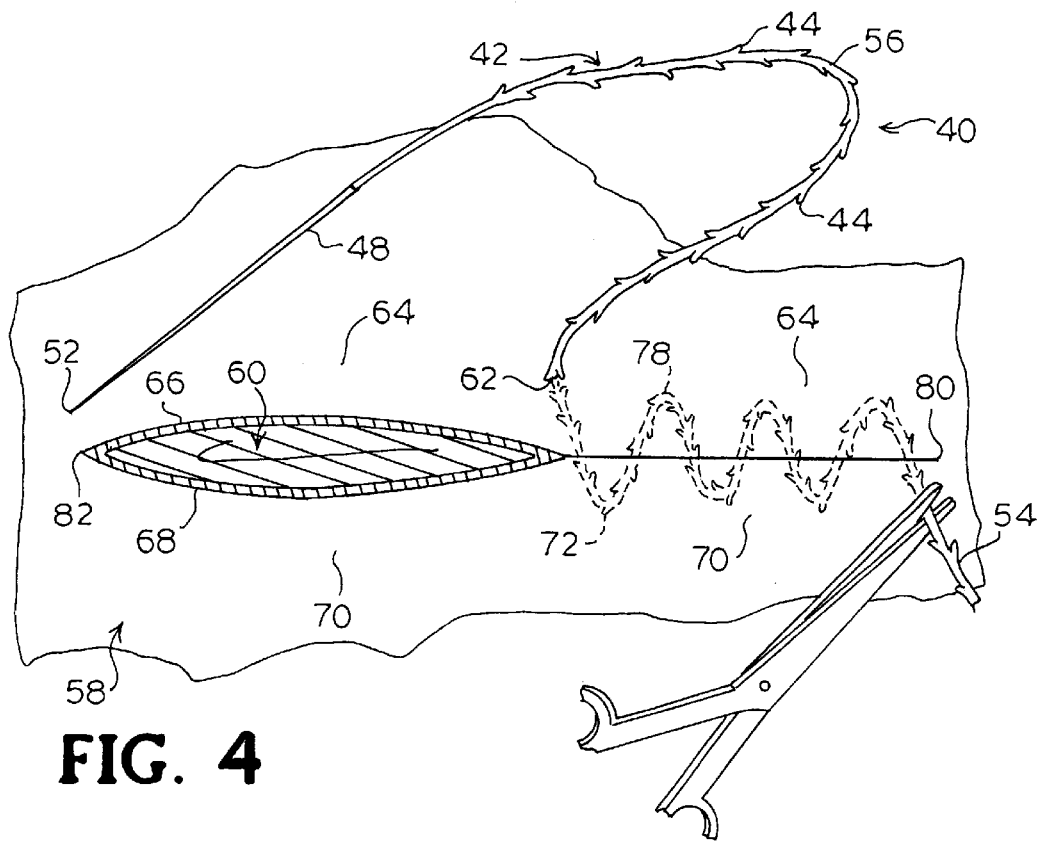

The previous steps are repeated with the first portion 54 of the suture 40 by inserting the needle 46 into the exit point 78 on the first side 64 of the wound 60 for advancing longitudinally in the first direction along the wound 60 in a "zigzag" pattern as shown in FIG. 4. The number of passes of the needle 46 is chosen in accordance with the size of the wound 60 and the strength required to hold the wound closed. The remaining length of the first portion 54 of the suture 40 protruding from the tissue at a first end 80 of the wound 60 is cut and discarded, leaving the remaining first portion 54 of the suture 40 in the tissue. The faces 66, 68 of the wound 60 are approximated by pushing the adjacent sides 64, 70 of the tissue together along the body 42 of the suture 40 in the tissue.

It is understood that the step of approximating the sides 64, 70 of the wound 60 can be performed as the suture 40 is advanced or after the end 80 of the wound 60 is reached. Moreover, we do not intend to limit ourselves to the depth of the suture paths shown in the FIGS. as the depth of the suture paths may be determined by the surgeon or the wound to be closed. Further, it is understood that straight ends 46, 48 of the suture may also produce more curved transitions as determined by the surgeon.

Figure 5:
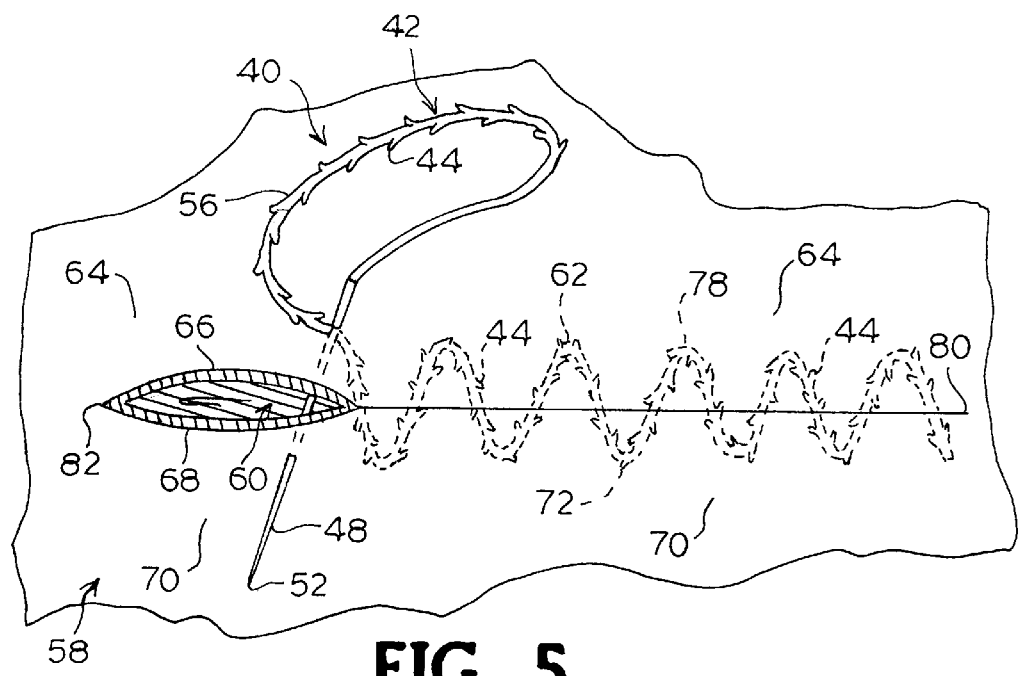
Figure 6:
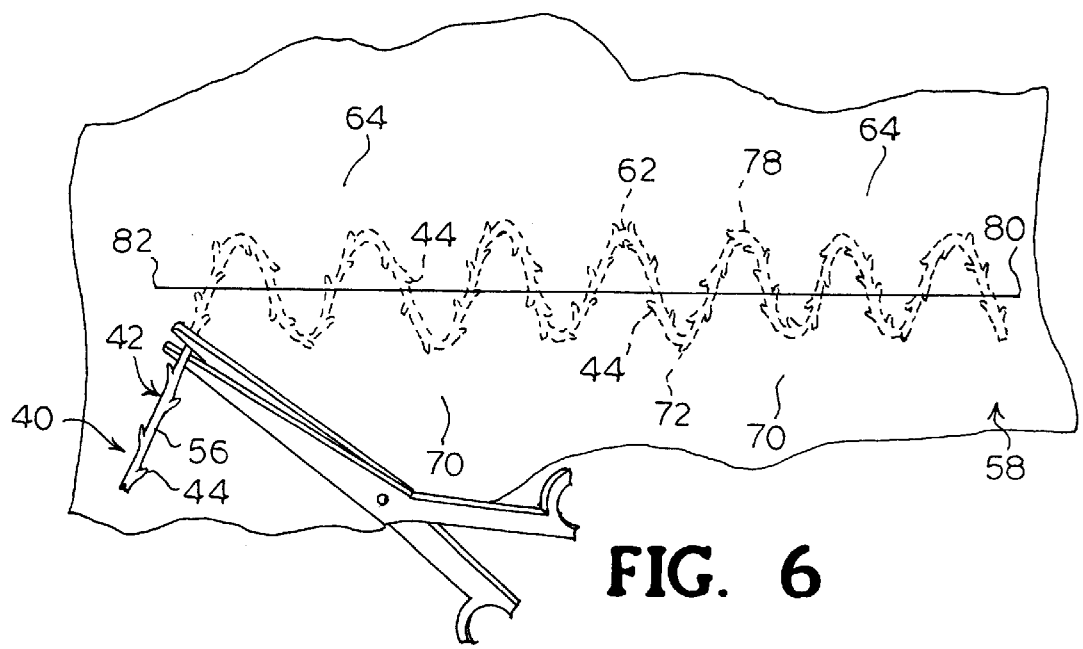

The surgeon repeats the steps of this procedure with the second needle 48 on the second portion 56 of the suture (FIG. 5). The initial insertion point 62 of the second needle 48 is at the same initial point of insertion 62 of the first needle 46 at the first side 64 of the wound 60. The surgeon thus advances the second portion 56 of the suture 40 into the tissue along the wound 60 in a direction toward the other end 82 of the wound 60 using the same zigzag pattern approximating the faces 66, 68 of the wound 60. The remaining length of the second portion 56 of the suture 40 protruding from the skin 58 at the end 82 of the wound 60 is then cut and discarded (FIG. 6).

An embodiment of the method for joining the sides of an open wound in tissue according to the present invention using a subcuticular stitch is shown in FIGS. 7–10. The tissue shown in the FIGS. includes an outer epidermis 84, dermis 86, fat 88, fascia 90 and muscle 92. By penetrating the subcutaneous layers only and not the outer skin 58 layer, a wound 60 can be closed to facilitate healing while minimizing scar tissue.

Figure 7:
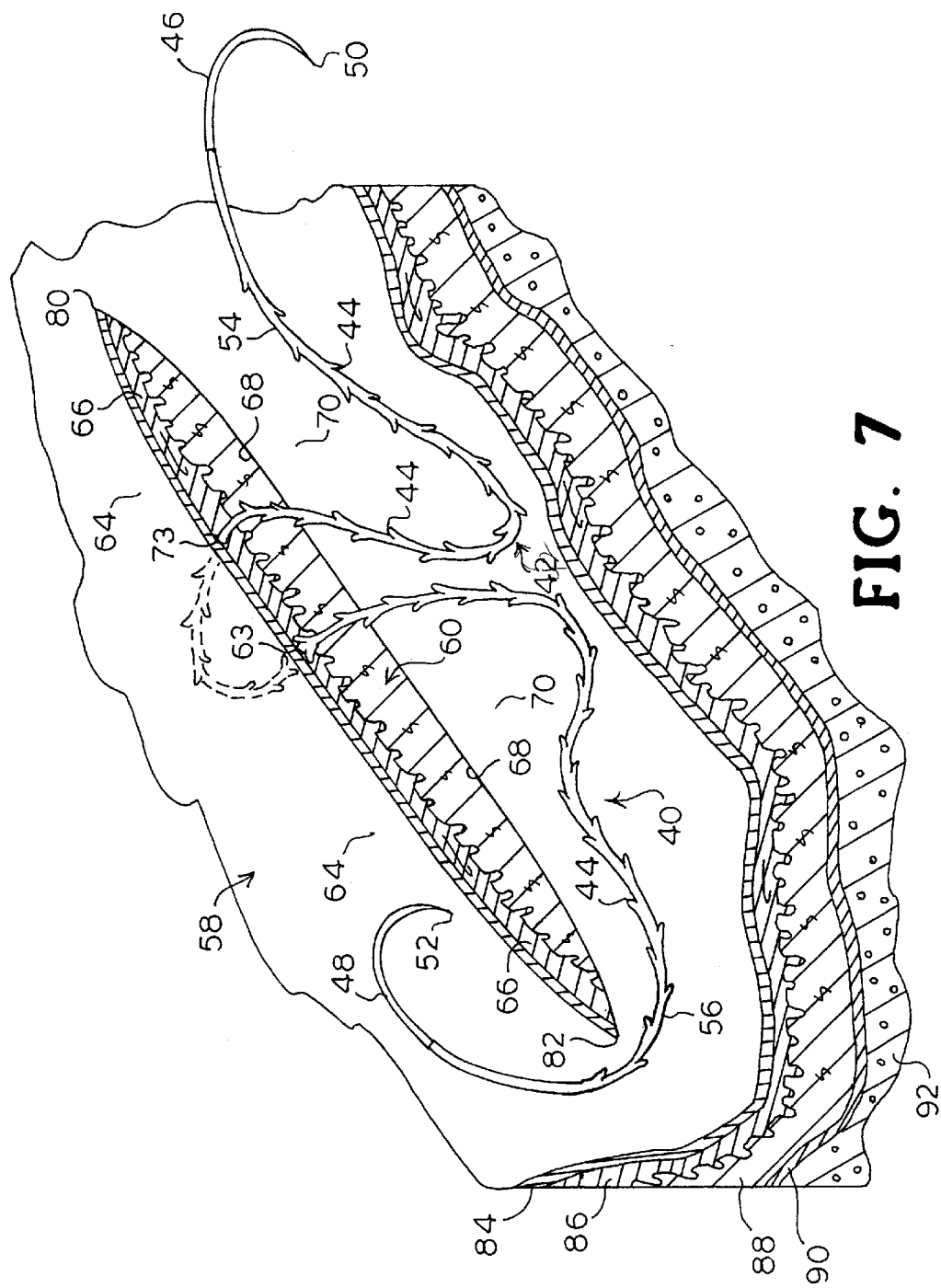
FIGS. 7–10 are perspective views of another embodiment of a method according to the present invention for joining two sides of an open wound in tissue.

Referring to FIG. 7, the subcuticular stitch method of the present invention uses a barbed suture 40 including curved ends 46, 48. The surgeon begins by inserting the first needle 46 into the tissue below the skin 58 surface at a face 66 on a first side 64 of the wound 60 at an initial insertion point 63 longitudinally spaced from the ends 80, 82 of the wound 60. The surgeon advances the needle 46 through the tissue along a curvilinear path until the point 50 of the needle 46 extends from the tissue at a subcutaneous exit point 73 in the first face 66 of the wound 60 longitudinally spaced toward one end 80 of the wound from the entry point 63 of the needle 46. The surgeon grips the needle 46 and pulls the needle 46 out of the tissue, drawing the first portion 54 of the suture 40 through the tissue until the barbs 44 on the second portion 56 engage the tissue at the insertion point 63 preventing further advancement of the suture 40 through the tissue. A length of the first portion 54 of the suture body 42 is thus positioned in the tissue along the selected curvilinear path as seen in FIG. 7.

Figure 8:
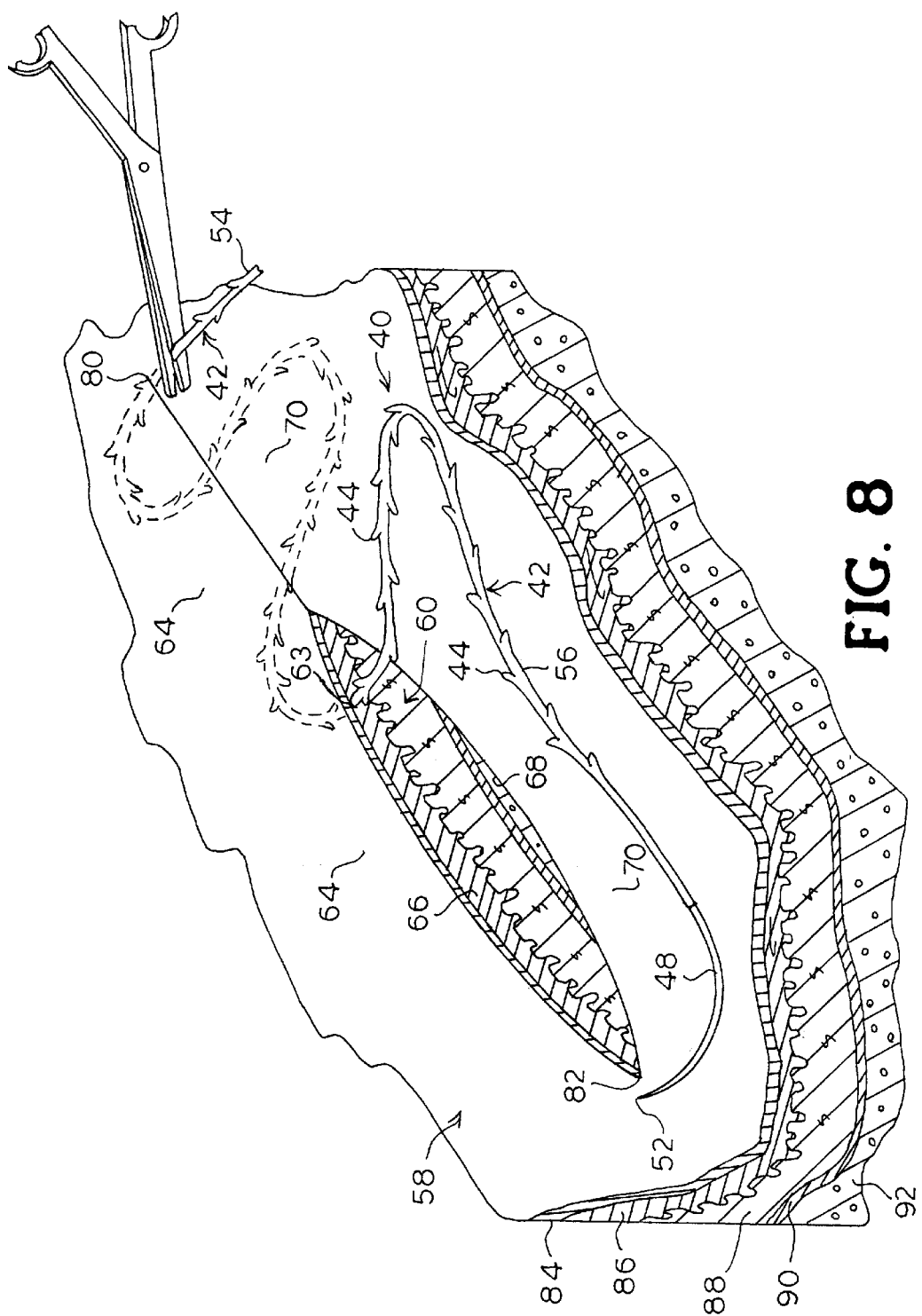

Turning to FIG. 8, the surgeon then inserts the needle 46 into the tissue at a subcutaneous entry point (not shown) in the face 68 at the second side 70 of the wound 60. The surgeon repeats the above steps of pushing the needle 46 through the tissue along a selected curvilinear path so that the point 50 of the needle 46 emerges from a subcutaneous exit point (not shown) in the second face 68 of the wound 60 longitudinally spaced toward the end 80 of the wound 60 from the entry point. The surgeon grips the needle 46 and draws the first portion 54 of the suture 40 into the tissue further along the wound 60. In this manner, the surgeon advances the first portion 54 of the suture 40 longitudinally along the wound 60 to the one end 80 of the wound in a wave-like or "sinusoidal" pattern. As noted above, the faces 66, 68 of the wound 60 are approximated as the surgeon progresses, or when the end 80 of the wound 60 is reached, by pushing the adjacent sides 64, 70 of the tissue together along the body 42 of the suture 40. The needle 46 along with remaining length of the first portion 54 of the suture 40 is drawn through the surface of the skin 58 at the one end 80 of the wound 60 is cut and discarded (FIG. 8).

Figure 9:
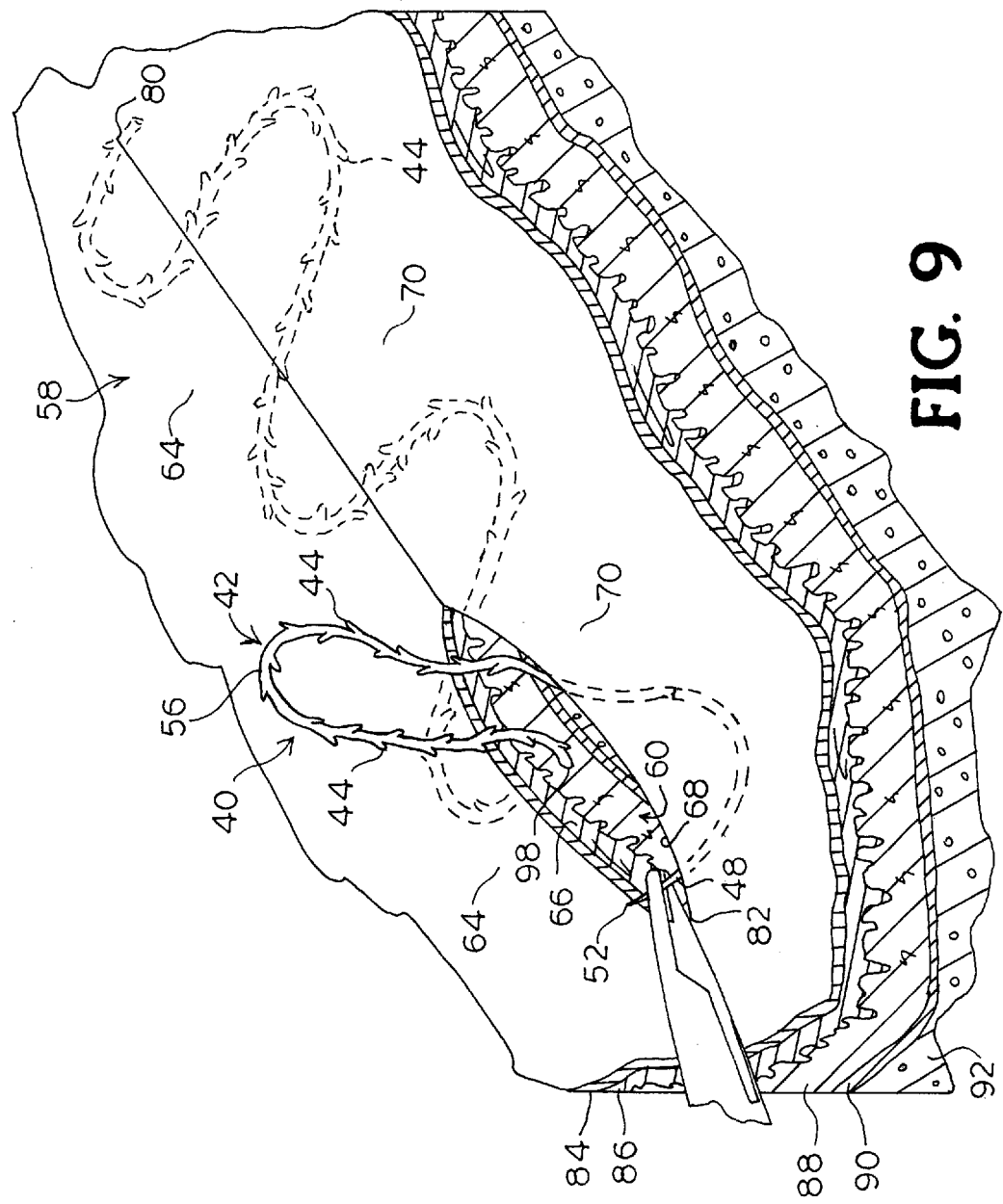
Figure 10:
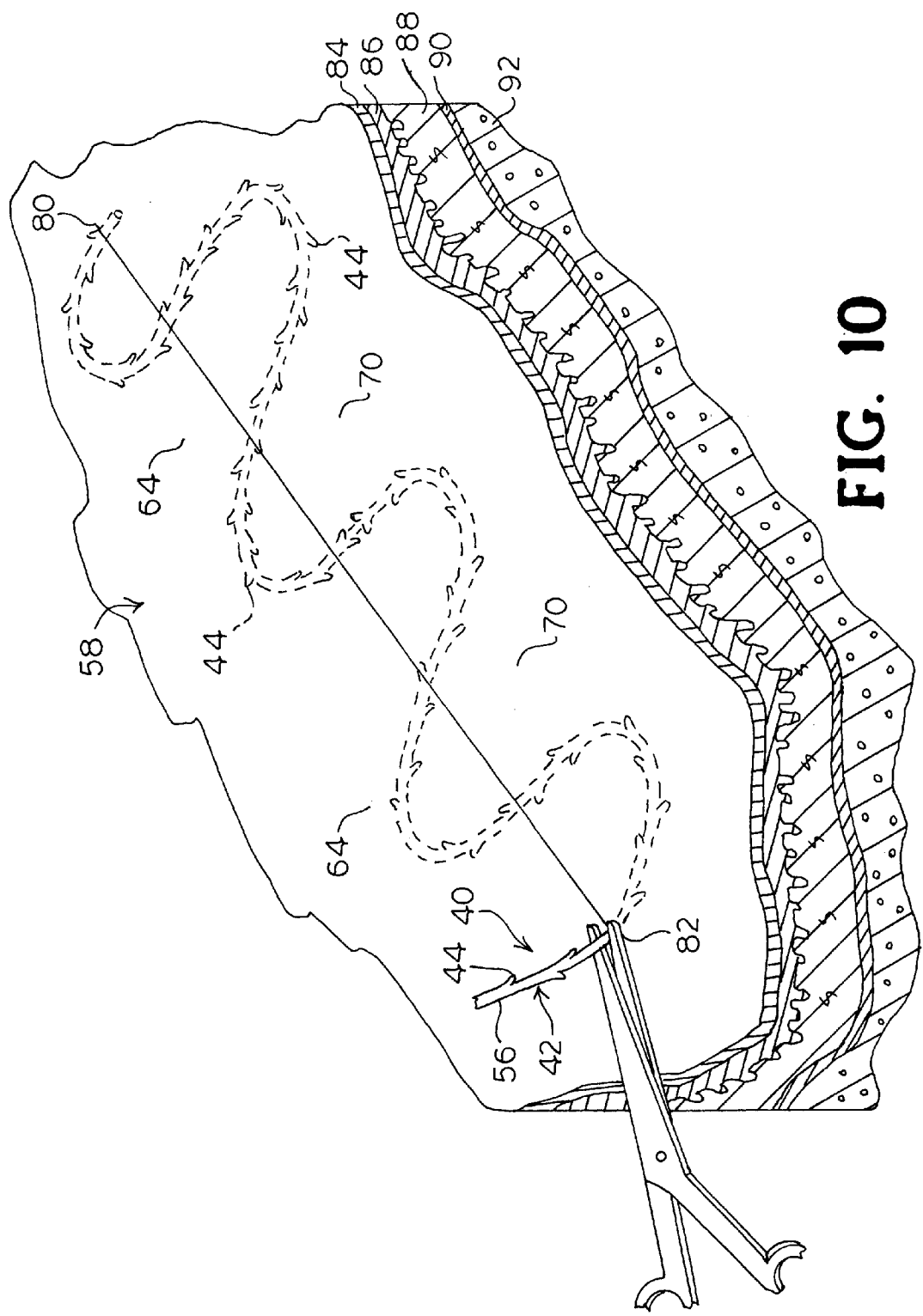

The surgeon repeats the procedure at the other end of the wound (FIG. 9) with the second portion 56 of the suture 40. The surgeon begins by inserting the second needle 48 into the tissue at a subcutaneous point (not shown) in the second face 68 of the wound 60. The surgeon advances the second needle 48 along a curvilinear path from the point of initial insertion toward the other end 82 of the wound 60 until the needle 48 emerges from a subcutaneous exit point (not shown) the second face 68 of the wound 60 longitudinally spaced from the initial entry point of the needle 48. The surgeon then pulls the needle 48 from the tissue, drawing the second portion 56 of the suture 40 into the tissue, and inserts the needle 48 into the first face 66 of the wound 60 at a subcutaneous entry point (not shown) at the first side 64 of the wound 60. Again, the surgeon advances the needle 48 along a curvilinear path until the needle 48 emerges from a subcutaneous exit point 98 in the face 66 further toward the other end 82 of the wound and draws the needle 48 and suture portion 56 through the tissue. FIG. 9 shows the needle 48 being drawn a second time from the second face 68 of the wound 60. Thus, the surgeon advances the second portion 56 of the suture in a sinusoidal pattern to the end 82 of the wound 60 (FIG. 10) and approximates the faces 66, 68 of the wound 60. The length of the second portion 56 of the suture body 42 protruding from the skin 58 at the end of the wound 60 is then cut and discarded.

Figure 11:
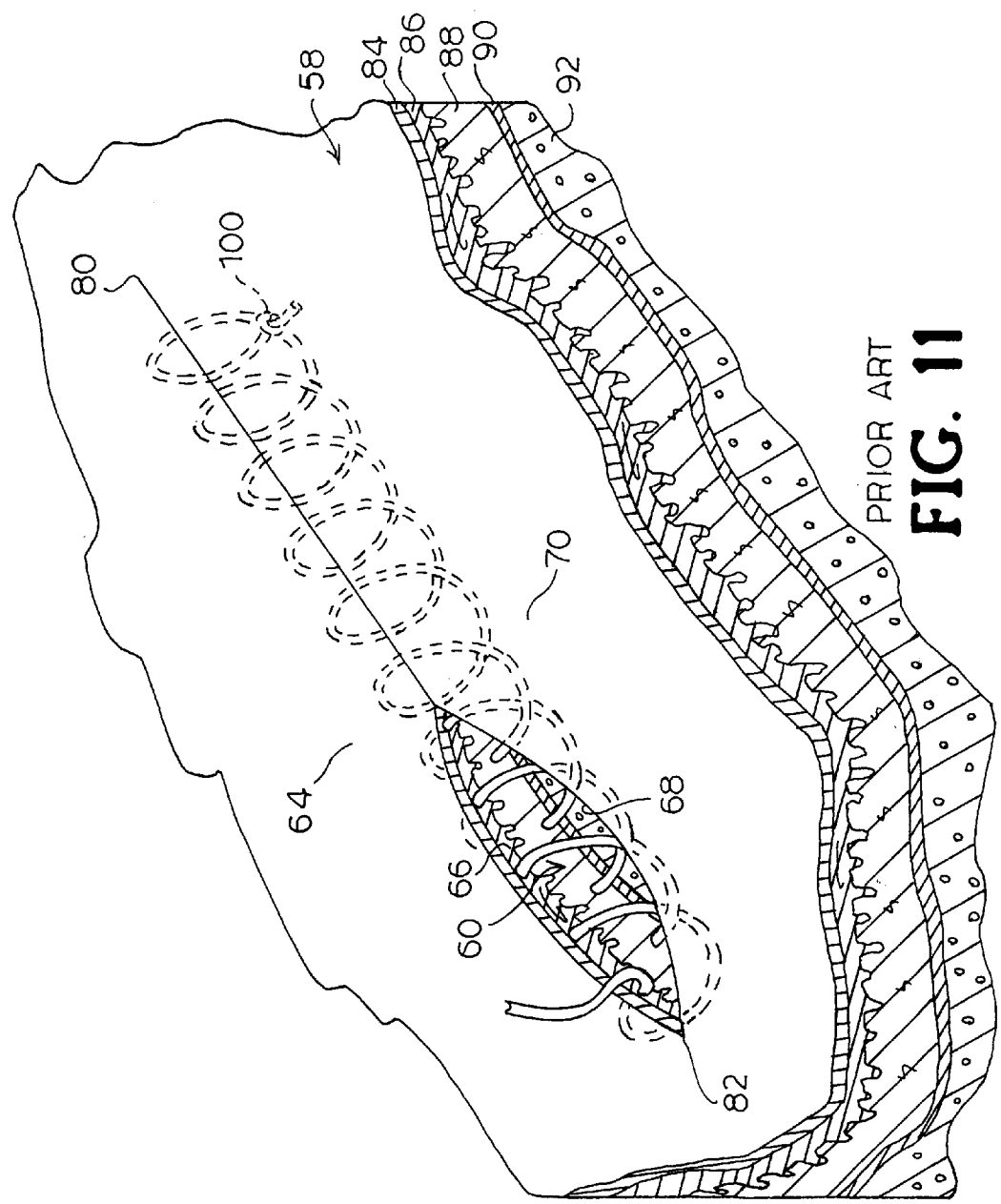
FIG. 11 is a perspective view of a prior art method for joining two sides of an open wound in tissue using a spiraling suture path.

FIG. 11 shows a prior art subcutaneous suturing method for closing a wound 60 using a spiraling, "corkscrew-shaped" stitch pattern. The surgeon begins at one end 80 of the wound by tying a knot 100 in the first loop and advancing the suture in a corkscrew pattern to the other end of the wound 82 where the suture is tied off. Tying the knots at the end and burying them, which is preferred by the surgeon, is technically very challenging, even more so when the incision is almost closed.

FIGS. 12–15 show a similar corkscrew-shaped stitch pattern for closing a wound 60 according to an embodiment of the method of the present invention. This embodiment is similar to the method described above using a subcutaneous sinusoidal stitch pattern.

Figure 12:
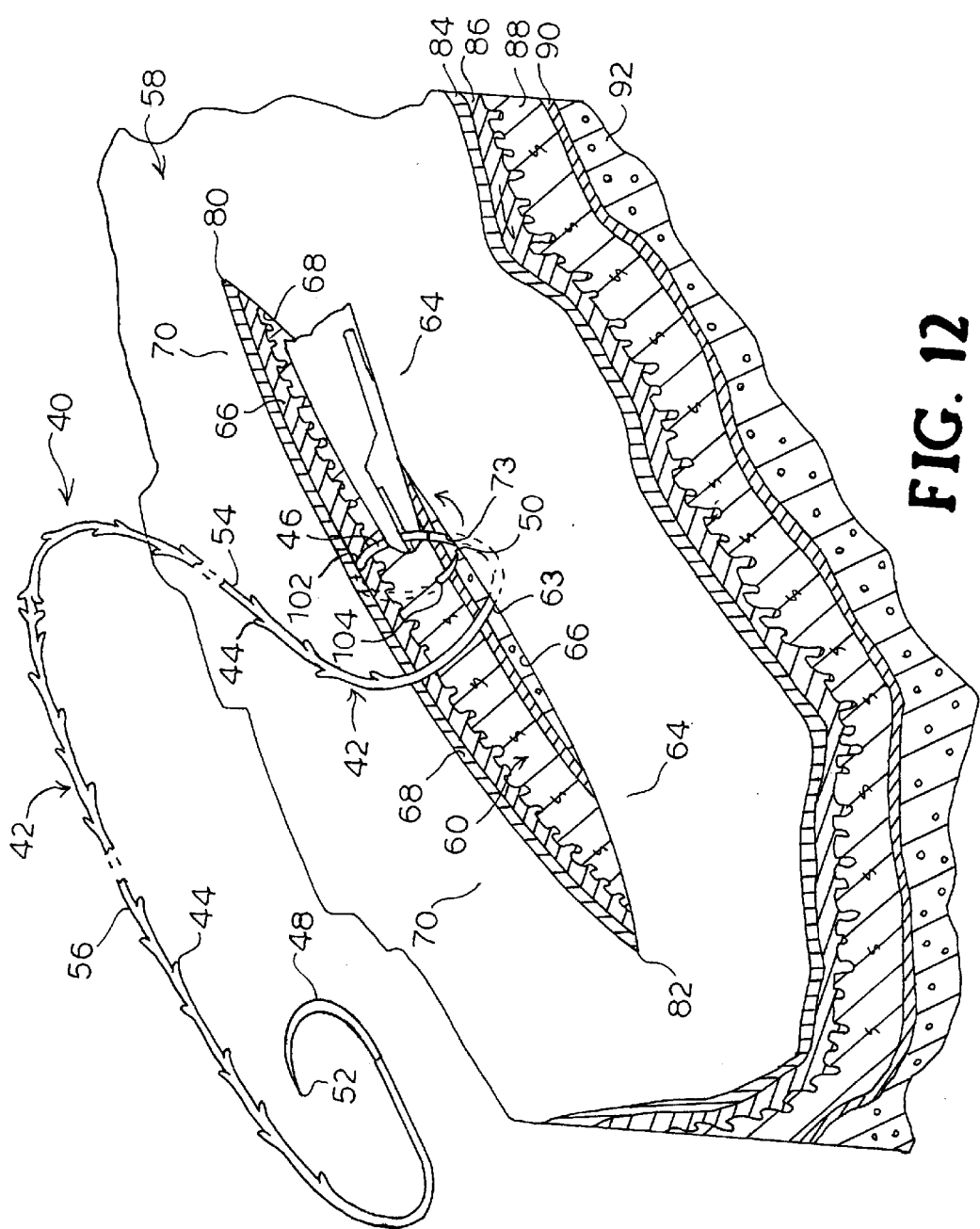
FIGS. 12–15 are perspective views of an embodiment of a method according to the present invention for joining two sides of an open wound in tissue using a spiraling suture path.
Figure 13:
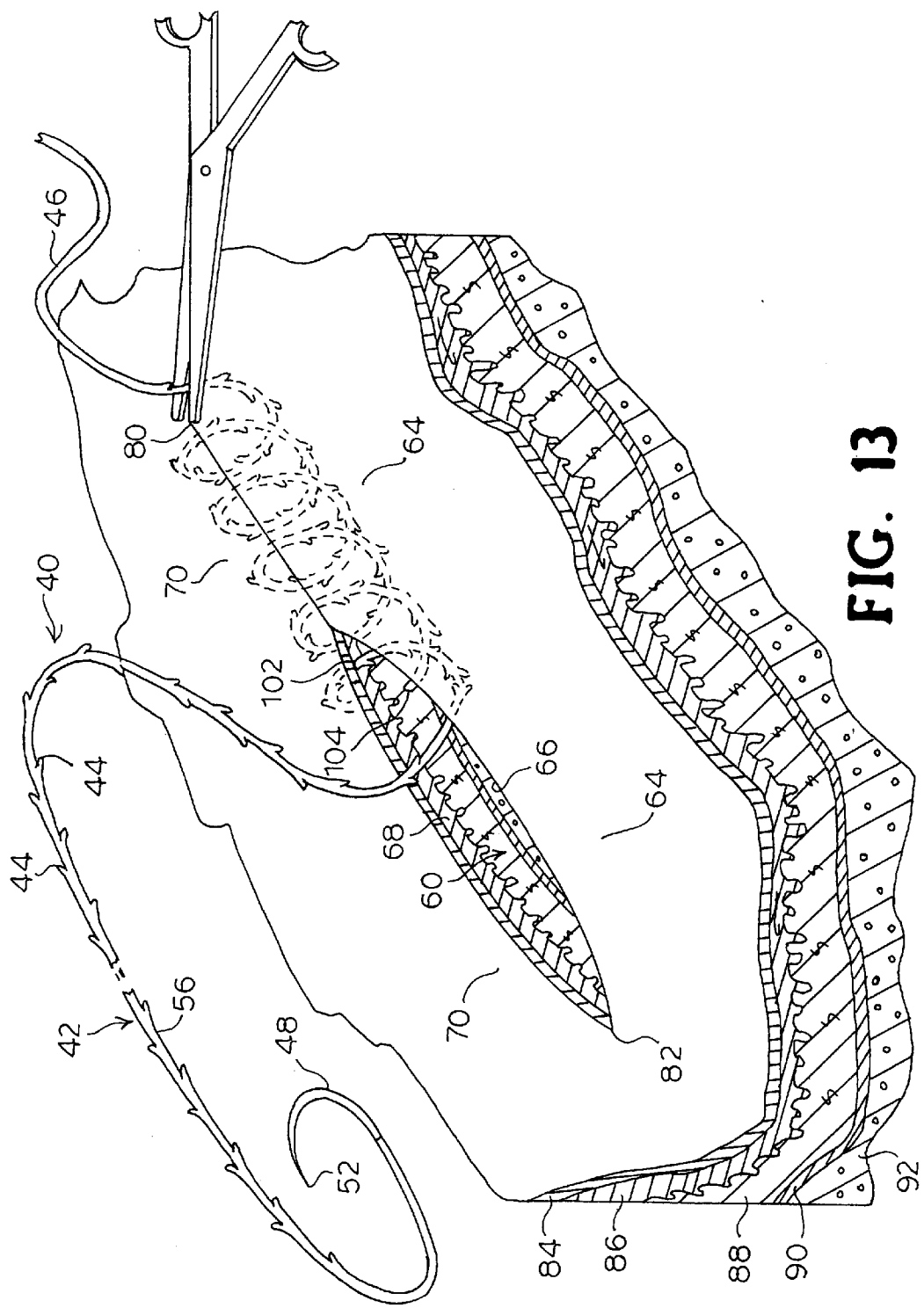

Referring to FIG. 12, the surgeon begins by inserting one of the needles 46 into the tissue below the skin 58 surface at a face 66 on a first side 64 of the wound 60 at an initial subcutaneous insertion point 63 longitudinally spaced from the ends 80, 82 of the wound 60. The surgeon advances the needle 46 upward through the tissue along a curvilinear path until the point 50 of the needle 46 extends from the tissue at a subcutaneous exit point 73 in the first face 66 of the wound 60 longitudinally spaced toward one end 80 of the wound and above the entry point 63 of the needle 46. The surgeon then inserts the needle 46 into the tissue at a subcutaneous entry point 102 in the face 68 at the second side 70 of the wound 60. The surgeon pushes the needle 46 through the tissue along a selected curvilinear path so that the point 50 of the needle 46 emerges from a subcutaneous exit point 104 in the second face 68 of the wound 60 longitudinally spaced toward the end 80 of the wound 60 and below the entry point 102. The surgeon repeats these steps (FIG. 13) for advancing the first portion 54 of the suture 40 longitudinally along the wound 60 to the one end 80 of the wound in the spiraling, corkscrew stitch pattern. It is understood that the number and diameter of coils can be varied as desired. At any selected convenient point, the surgeon grips the needle 46 for drawing the first portion 54 of the suture 40 through the tissue until the barbs 44 on the second portion 56 engage the tissue at the insertion point 63 preventing further advancement of the suture 40 through the tissue. The surgeon approximates the faces 66, 68 of the wound 60 as the surgeon progresses or when the end 80 of the wound 60 is reached as described above. The remaining length of the first portion 54 of the suture 40 is drawn through the surface of the skin 58 at the one end 80 of the wound 60 and cut and discarded.

Figure 14:
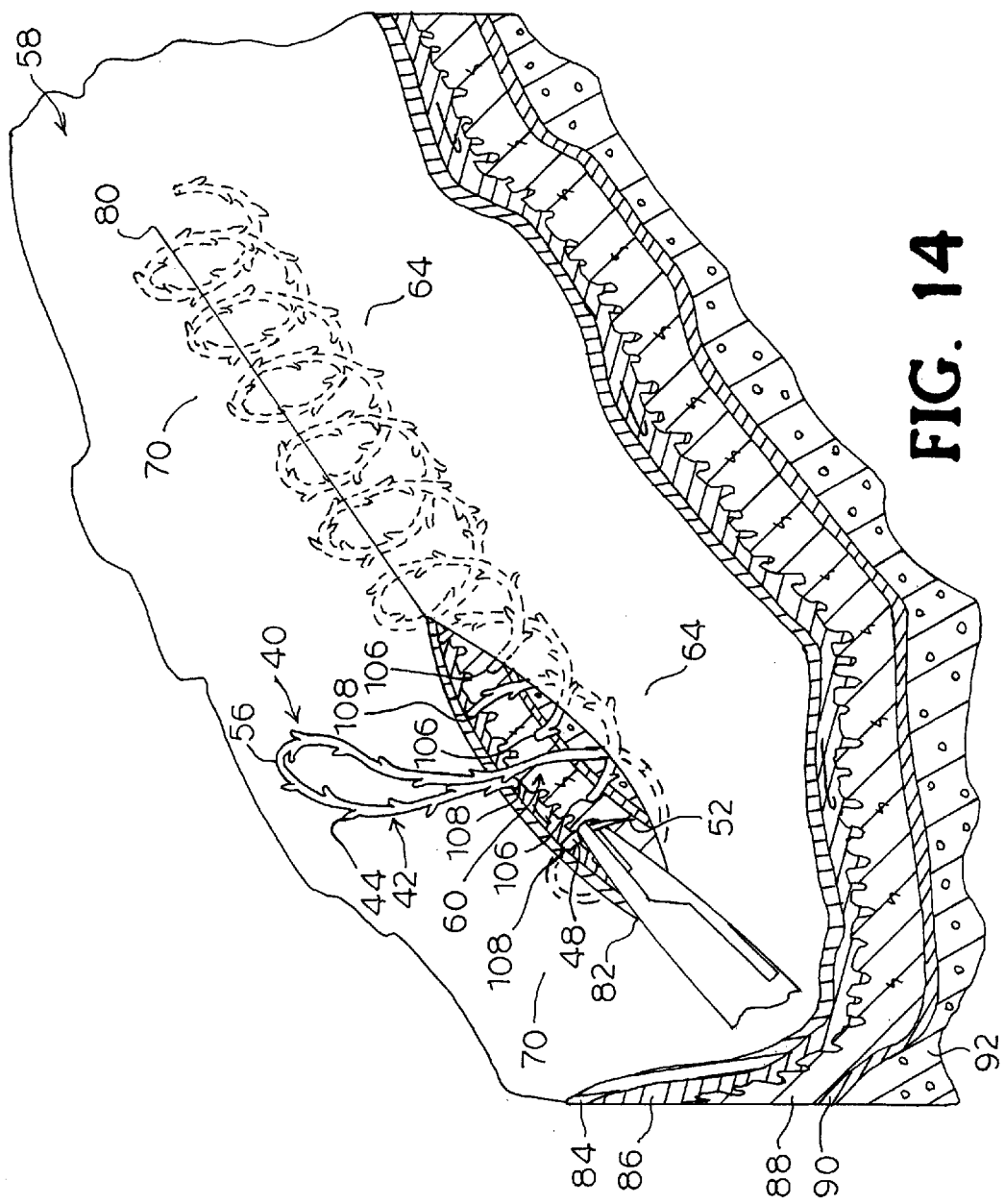
Figure 15:
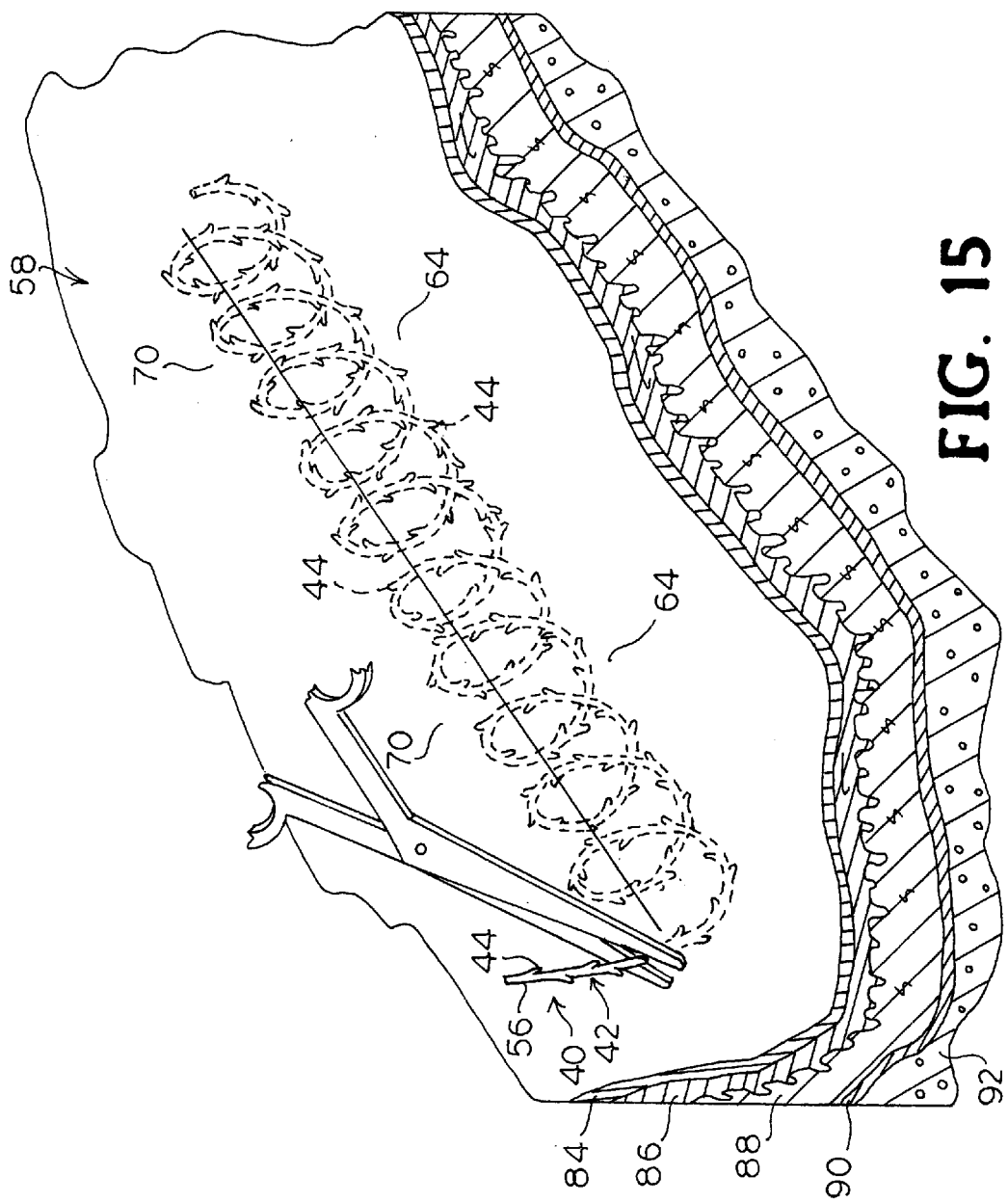

The surgeon repeats the procedure at the other end 82 of the wound 60 with the second portion 56 of the suture 40. As seen in FIG. 14, several "coils" of the second portion 56 of the suture 40 have been entered into the tissue in a direction toward the other end 82 of the wound 60. Subcutaneous entry points 106 and exit points 108 in the faces 66, 68 of the wound 60 are visible. The surgeon advances the second portion 56 of the suture 40 to the end 82 of the wound 60 (FIG. 15) and approximates the faces 66, 68 of the wound 60. The length of the second portion 56 of the suture body 42 protruding from the skin 58 at the end of the wound 60 is then cut and discarded.

Figure 16:
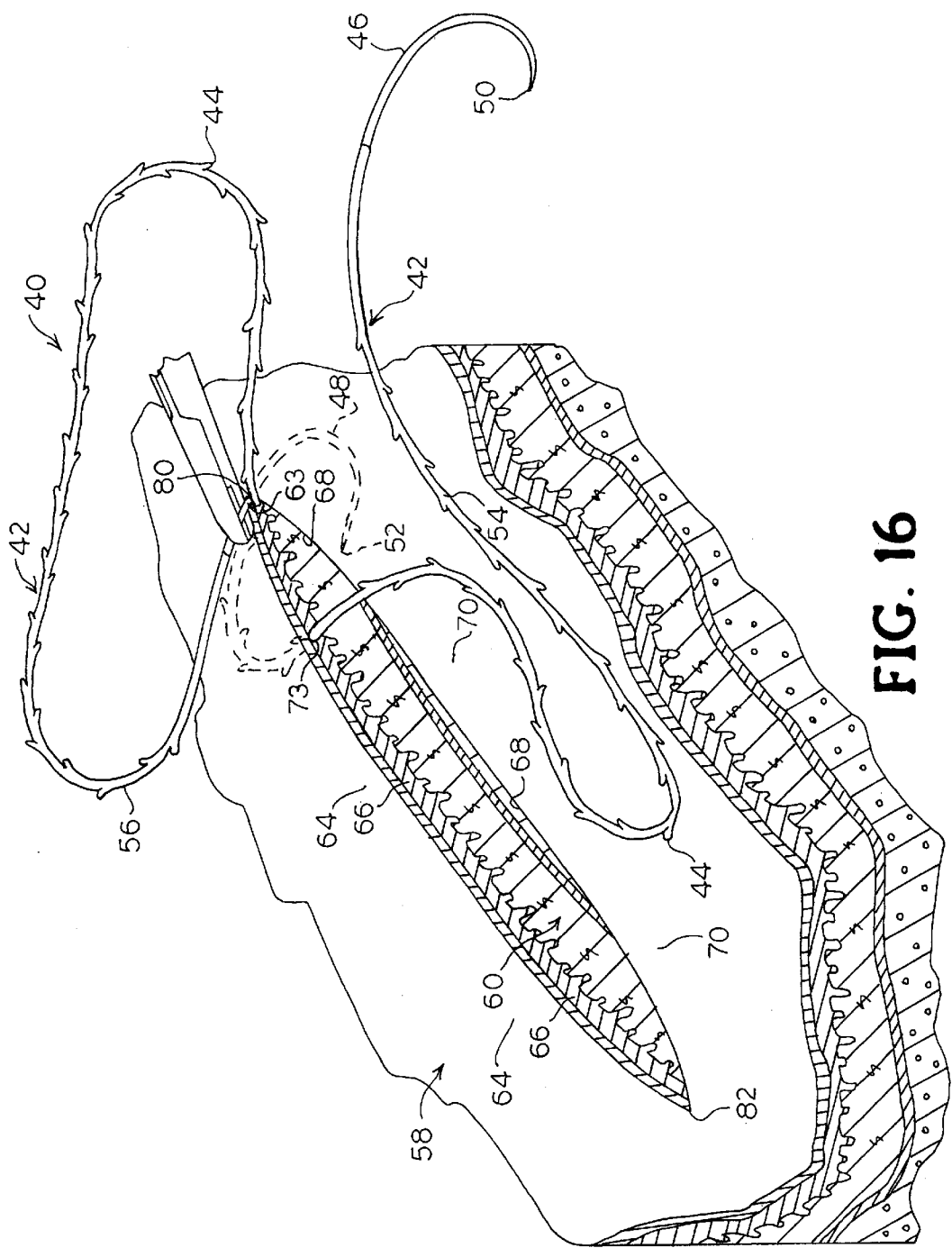
FIGS. 16–18 are perspective views of still another embodiment of a method according to the present invention for joining two sides of an open wound in tissue.
Figure 17:
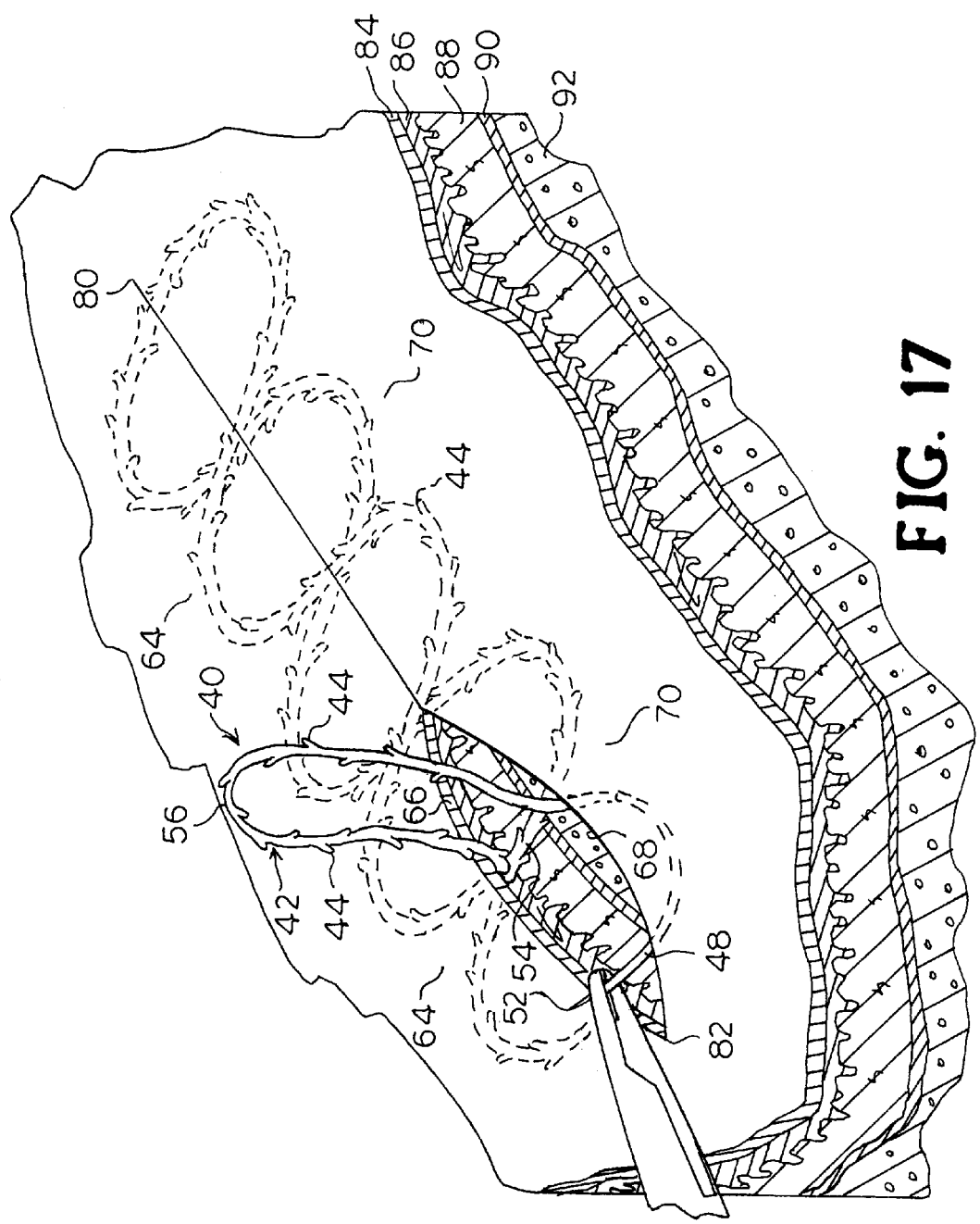
Figure 18:
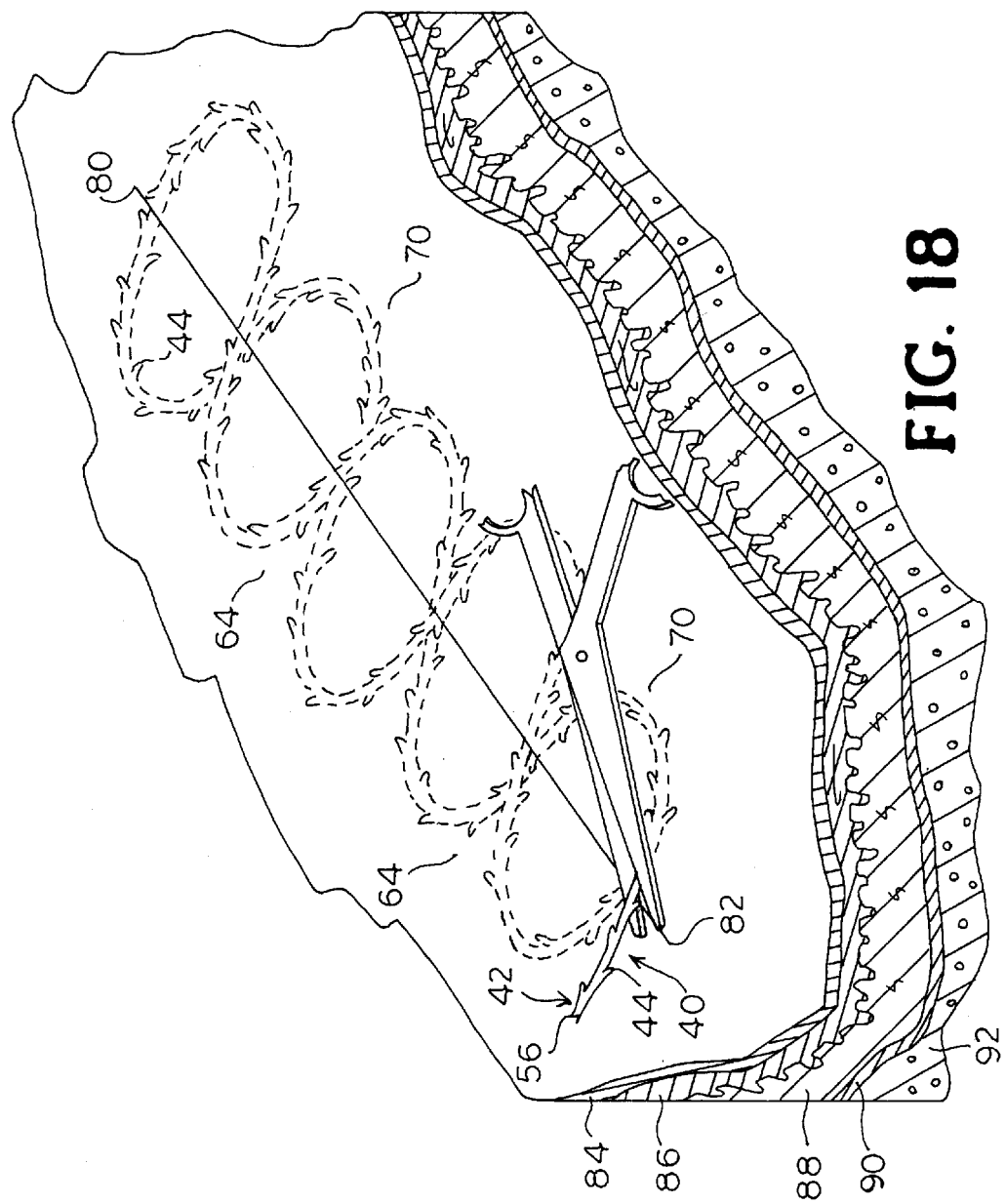

Another embodiment of a subcutaneous suturing method for joining and holding closed an open wound 60 in tissue according to the present invention is shown in FIGS. 16–18. This method also uses a barbed suture 40 having curved pointed ends 46, 48, such as surgical needles.

Referring to FIG. 16, the surgeon begins by inserting the first needle 46 subcutaneously into the tissue at a face 66 on a first side 64 of the wound 60 at an initial insertion point 63 adjacent one end 80 of the wound 60 and pushes the needle 46 through the tissue along a selected curvilinear path until the needle 46 extends from the tissue at a subcutaneous exit point 73 in the first face 66 of the wound 60 longitudinally spaced from the end 80 of the wound 60 in a direction toward the other end 82 of the wound 60. The surgeon grips the needle 46 and pulls the needle 46 out of the tissue for drawing the first portion 54 of the suture 40 including barbs 44 for resisting movement in the opposite direction through the tissue until the barbs 44 of the second portion 56 engage the first face 66 of the wound 60 at the insertion point 63 preventing further advancement of the suture 40 into the tissue. A length of the first portion 54 of the suture body 42 is thus positioned in the tissue along the selected curvilinear path.

As further seen in FIG. 16, the surgeon next inserts the second surgical needle 48 into the tissue at a subcutaneous entry point (not shown) in the face 68 at the second side 70 of the wound 60 substantially opposite the initial point of insertion 63 of the first needle 46 at the one end 80 of the wound 60. The surgeon advances the second needle 48 through the tissue along a selected curvilinear path until the needle 48 extends from the tissue at a subcutaneous exit point (not shown) in the second face 68 of the wound 60. The surgeon then pulls the second needle 48 for drawing the second portion 56 of the suture 40 through the tissue, including barbs 44 for resisting movement in the opposite direction, leaving a length of the second portion 56 of the suture 40 in the tissue at the end 80 of the wound 60.

The surgeon repeats the above steps with the first needle 46 and second needle 48 at the second and first sides 64, 70, respectively, of the wound 60. In this manner, the surgeon advances the suture 40 longitudinally along the wound 60 from the one end 80 of the wound to the other 82 in a "shoelace" pattern. As seen in FIG. 17, several passes of the suture 40 have been entered into the tissue of the wound 60. The faces 66, 68 of the wound 60 are approximated as the surgeon progresses, or when the end 82 of the wound 60 is reached, by pushing the adjacent sides 64, 70 of the tissue together along the body 42 of the suture 40. The lengths of the first portion 54 and second portion 56 of the suture 40 protruding from the skin 58 are cut and discarded (FIG. 18).

It is understood that the method of the present invention shown in FIGS. 7–10 can be used to generate a similar stitch pattern if a second suture is used which is entered in the tissue to mirror the path of the first suture.

Figure 19:
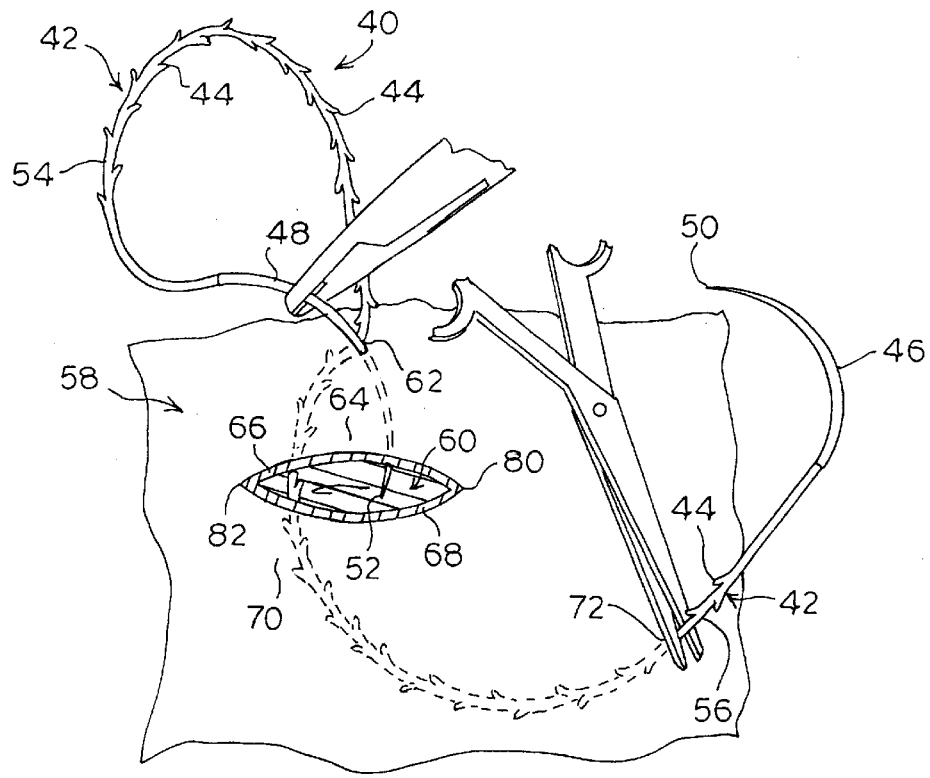
FIGS. 19 and 20 are plan views of a further embodiment of a method according to the present invention for joining two sides of an open wound in tissue.
Figure 20:
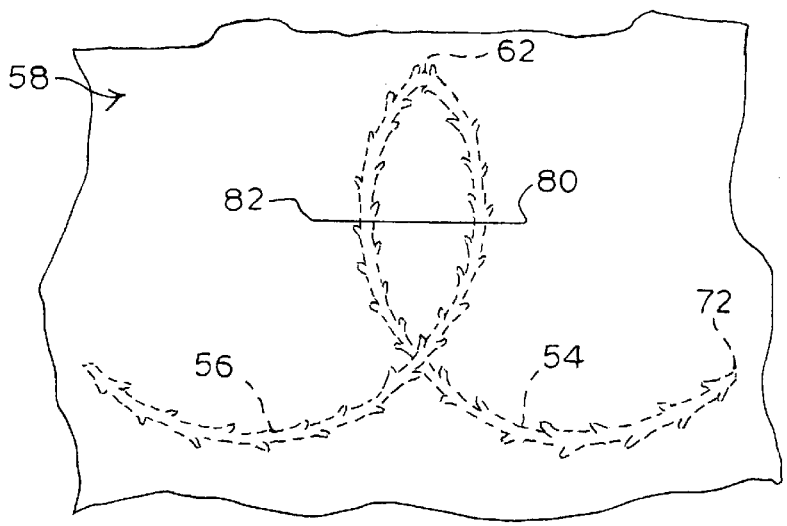

Another embodiment of the method according to the present invention for joining the sides 64, 70 of tissue in an open wound 60 is shown in FIGS. 19 and 20. In this embodiment, the surgeon inserts a first curved or straight end 46 of the suture 40, such as a needle, into the tissue at a point 62 on a first side 64 of the wound 60 and laterally spaced from the face 66 of the wound 60 at the first side 64. The surgeon advances the needle 46 through the tissue along a curvilinear path until the needle 46 emerges from the tissue on a second side 70 of the wound at an exit point 72 laterally spaced from the face 68 of the second side 70 of the wound 60 and longitudinally spaced in a first direction from the point of insertion 62. This path subcutaneously passes through both faces 66, 68 of the wound 60. The surgeon grips the needle 46 and pulls the needle 46 out of the tissue for drawing the first portion 56 of the suture 40 through the tissue until the barbs 44 of the second portion 56 engage the surface of the skin 58 at the insertion point 62 preventing further advancement of the suture 40 into the tissue. The faces 66, 68 of the wound 60 are approximated by pushing the adjacent sides 64, 70 of the tissue together along the body 42 of the suture 40 in the tissue. The length of the first portion 54 of the body 42 of the suture 40 protruding from the skin 58 is cut and discarded (FIG. 19).

The surgeon then inserts the second needle 48 into the tissue at the point of insertion 62 of the first needle 46 at the first side 64 of the wound 60. The surgeon pushes the needle 48 through the tissue along a curvilinear path which substantially mirrors the passage of the first needle 46 until the needle 48 emerges from the tissue at an exit point 110 laterally spaced from the wound and longitudinally spaced in a second direction from the point of insertion 62 such that the paths of the first and second portions 54, 56 of the suture 40 overlap. Again, the path of the second needle 48 subcutaneously passes through the faces 66, 68 of the wound 60. The surgeon grips the second needle 48 and pulls the needle 48 from the tissue for drawing the second portion 56 of the suture 40 into the tissue. The length of the second portion 56 of the suture 40 protruding from the skin 58 is cut and discarded, leaving a stitch in the tissue which resembles the Greek letter alpha (FIG. 20).

This stitch has its greatest benefit in small wound and incision closure. The alpha-shaped stitch can be placed quickly in tissue as compared with conventional loop sutures. Moreover, this stitch pattern has no blood constricting loops, leaves no stitch marks on the surface of the skin, does not have to be removed from the patient if bioabsorbable material is used. Two or more of the alpha-shaped stitches may be used to close a larger wound.

Figure 21:
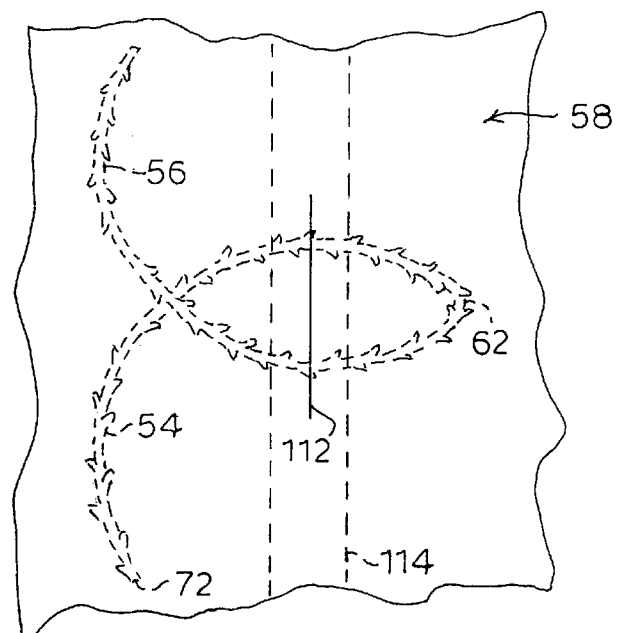
FIG. 21 is a plan view of the embodiment shown in FIGS. 19 and 20 for use in closing a vascular puncture via cinching of tissues directly above the vessel.
Figure 22:
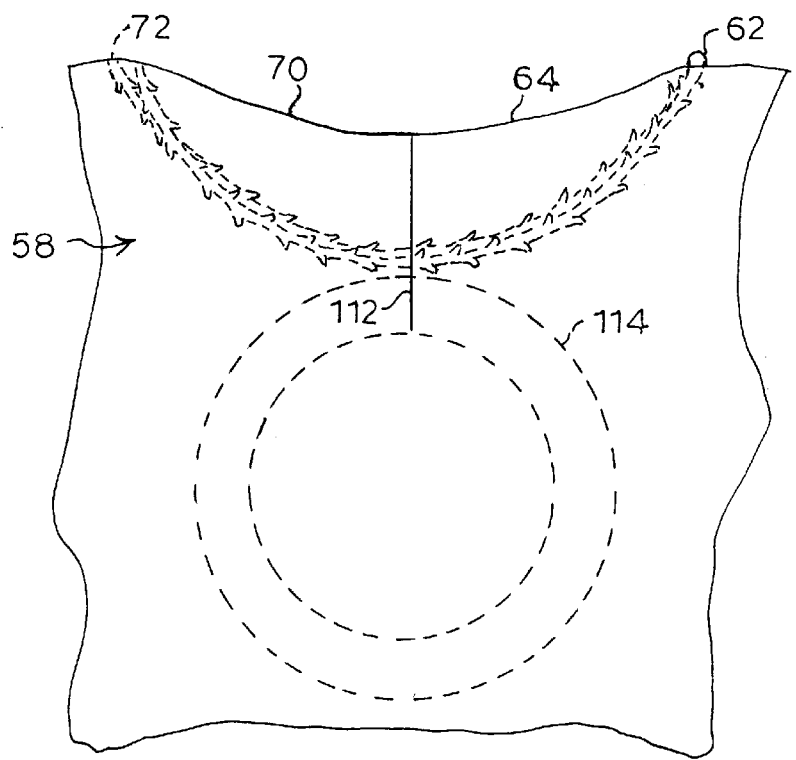
FIG. 22 is a cross-sectional view of the method shown in FIG. 21.

A particular application of the alpha-stitch according to the method of the present invention is as a means of restricting bleeding from an arterial opening by constricting the tissue above and around the arterial opening. For example, the introduction and removal of catheters into the femoral artery is typically required when performing cardiac catheterization, percutaneous interventions, and other vascular procedures. These puncture wounds are typically self-sealing after several hours of sustained external pressure at and around the insertion site of the puncture wound. FIGS. 21 and 22 show the alpha-stitch according to a method of the present invention positioned for performing this function. Note that the path of the suture portions 54, 56 is curvilinear with the respect to the skin 58 surface and that the deepest points of the arcs pass immediately above the puncture site 112 in the artery 114. In this embodiment, the ends 46, 48 of the suture 40 are pulled to put tension in the tissue. As the ends 46, 48 of the suture 40 are pulled, the tissue embraced by the suture is pulled both inward from the areas lateral to the artery 114 and downward from areas immediately above the artery 114. This constriction of tissue increases the density of tissue around the arterial puncture site 112 and imparts forces with vectors directed toward the arteriotomy site to limit bleeding. Further, this suture method avoids the need to traverse the artery wall or lumen, thus eliminating the risk of vessel wall dissection and promoting introgenic thrombogenesis.

The method of the present invention is also useful in binding together partially or completely severed tendons or other internal tissue repairs requiring considerable tensile strength. For example, referring to FIG. 23, a finger 120 is shown with a portion of the outer layer of tissue cut-away to schematically show a severed tendon 122. A Kessler suturing method for joining the two ends 124, 126 of the tendon 122 is shown in FIG. 24. This method requires the surgeon to apply an intricate stitch pattern and to complete the tendon connection with one or two technically challenging knots 128. No portion of the suture knot 128 may protrude from the outside surface of the repaired tendon 122 where it could snag the surrounding tendon sheath and impede healing. The knot 128 also presents a particular dilemma since it must be tied between the two ends 124, 126 of the tendon 122, where it can be a barrier between tendon sections that must appose in order to effectively heal. A further limitation of the conventional tendon repair method is that relatively small amounts of tension can stretch the tendon 122, allowing it to slide along the smooth monofilament fiber and effectively disrupt, or in the case of greater amounts of tension, separate completely at the wound margin. This outcome substantially limits healing even though the suture material remains intact.

Figure 25:
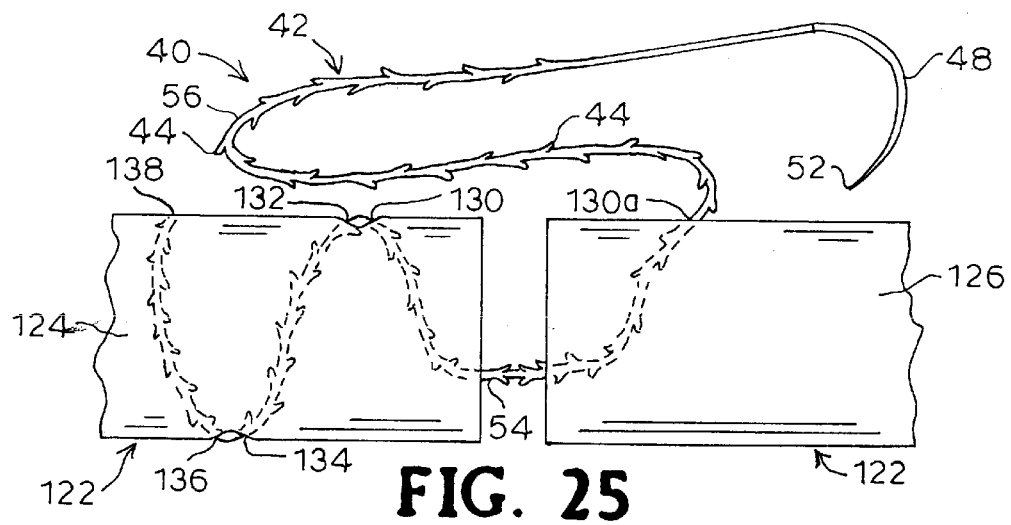

A method according to the present invention for joining the two ends 124, 126 of the tendon 122 is shown in FIGS. 25–28. Referring to FIG. 25, the surgeon begins by inserting the first end 46 of the suture 40, which may a straight or curved surgical needle, into one end 124 of the tendon 122 and pushing the needle 46 through the tendon 122 along a selected curvilinear path until the point 50 of the needle 46 extends from an exit point 130 in the periphery of the tendon 122 longitudinally spaced from the one end of the tendon 122. The first needle 46 is gripped and pulled out of the tendon for drawing the first portion 54 of the suture 40 through the tendon 122 leaving a length of the first portion 54 of the suture in the tendon end 124 between the end of the tendon 122 and the exit point 130. The surgeon reinserts the needle 46 into the periphery of the tendon 122 at an entry point 132 immediately adjacent the exit point 130 and pushes the needle 46 along a selected curvilinear path until the point 50 of the needle 46 exits the other side of the tendon at an exit point 134 that is longitudinally spaced from the entry point 132. It is understood that the surgeon could use the exit point 130 as the next entry point for the needle 46 if desired. The surgeon pulls the needle 46 out of the tendon for drawing the first portion 54 of the suture 40 through the tendon 122, reinserts the needle 46 into the side of the tendon 122 at an entry point 136 immediately adjacent the exit point 134 and pushes the needle 46 along a selected curvilinear path back out of the other side of the tendon 122 at an exit point 138 longitudinally spaced from the previous entry point 136. It is understood that the surgeon makes as many passes as deemed necessary for holding the end 124 of the tendon 122, or as the length or thickness of the tendon 122 allows, and removes the remaining length of the first portion 54 of the suture 40.

Figure 26:
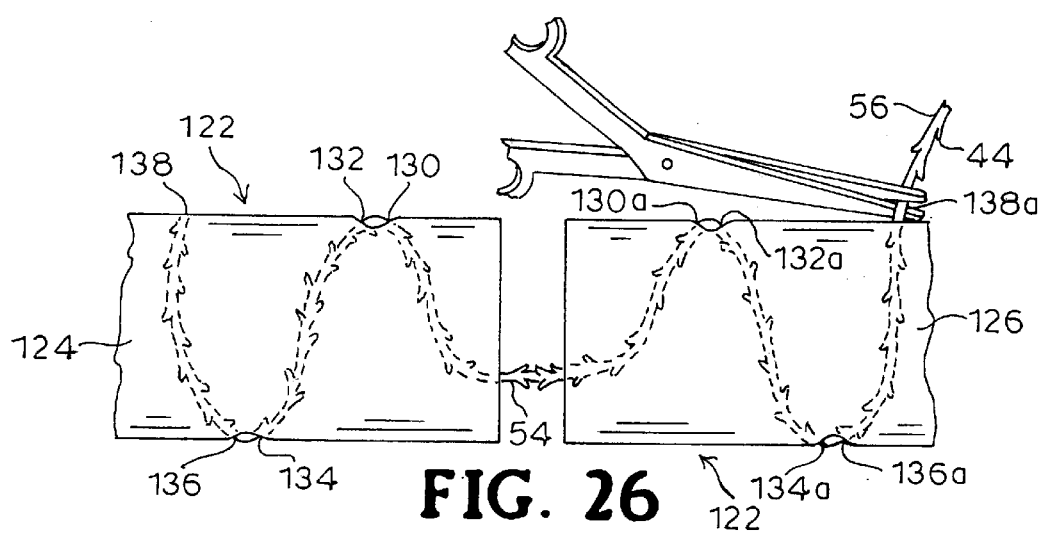

As seen in FIG. 26, these steps are repeated with the second portion 56 of the suture 40 at the other end 126 of the tendon 122. The pattern of the second portion 56 of the suture 40 in the second end 126 of the tendon 122 generally mirrors the first portion 54 of the suture 40 in the first end 124 of the tendon 122, including exit points 130*a*, 134*a*, 138*a* and entry points 132*a*, 136*a*. The ends 124, 126 of the tendon 122 are brought together while maintaining tension on the free ends of the sutures.

Figure 27:
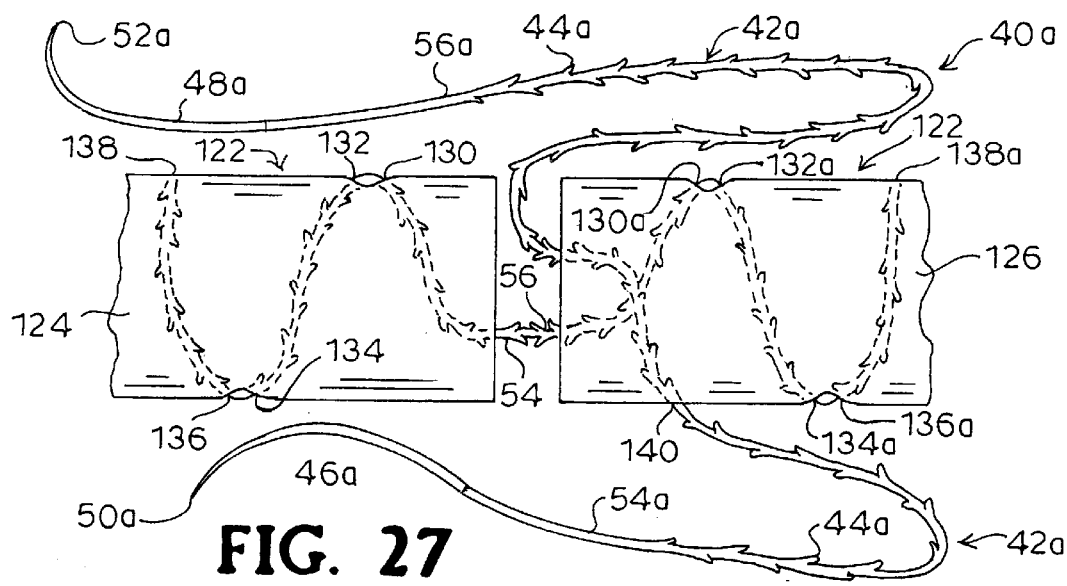

Referring now to FIG. 27, a second suture 40*a* is introduced at the second end 126 of the tendon 122. The first needle 46*a* of the second suture 40*a* is inserted into the end 126 of the tendon 122 and pushed through the tendon 122 along a selected curvilinear path until the needle 46*a* extends from an exit point 140 in the periphery of the tendon 122 substantially opposite the first exit point 130*a* of the second portion 56 of the first suture 40. The needle 46*a* of the second suture 40*a* is pulled out of the tendon 122 for drawing the first portion 54*a* of the second suture 40*a* through the tendon 122 leaving a length of the suture 40*a* in the tendon 122 between the end 126 of the tendon 122 and the exit point 140. The surgeon repeats the steps described above by reinserting the needle 46*a* into the tendon 122 at an entry point 142 (FIG. 28) adjacent the exit point 140 and pushing the needle 46*a* along a selected curvilinear path until the needle 46*a* emerges from an exit point 144 in the periphery of the tendon 122 substantially opposite the second exit point 134*a* of the second portion 56 of the first suture 40. In this manner, the surgeon advances longitudinally along the end 126 of the tendon 122 entering at 146 and exiting at 148. The previous steps are repeated at the other end 124 of the tendon 122 with the second portion 56*a* of the second suture 40*a*. The number of sutures used depends on the size, caliber, and length of the tendon to be repaired. Big tendons will require more than two sutures whereas one may suffice for very small tendons.

Tendon repair with two sutures according to the present invention exhibits equivalent or better holding power as the prior art technique. Moreover, tendons repaired according to the methods of the present invention maintain their original configuration, profile, contour, and form better when being stretched.

The invention is further illustrated by the following non-limiting examples.

EXAMPLE 1

A straight incision wound, about 1.5 cm deep, was created in each of four samples of cadaveric porcine skin tissue. The tissue samples measured 4 cm by 10 cm. Each incision was centered on the skin sample so that the wound was 4 cm long from end to end.

Each wound was closed according to a different suture method using identical barbed sutures made from monofilament PDS (polydioxanone) size 0. One wound was closed according to the method shown in U.S. Pat. Nos. 5,342,376 and 6,241,747, without using the inserting device ("the Ruff method"). Seven sutures were placed along the length of the wound and running generally perpendicularly to the faces of the wound. When placed, the sutures dipped below the incision line thus engaging subcutaneous tissue below the incision and the ends of the sutures engaged some dermis. A second wound was closed using seven needle-tipped sutures placed along the length of the wound in the dermis and running generally perpendicularly to the faces of the wound similar to the method shown in U.S. Pat. No. 5,931,855 ("the Buncke method"). In both methods, the length of each suture buried under the skin was approximately 6 cm. A third wound was closed using the "zigzag" stitch pattern in the dermis as described above and shown in FIGS. 3–6. The number of passes resulted in four entry/exit points on each side of the wound. A fourth wound was closed using the corkscrew-shaped stitch pattern described above and shown in FIGS. 12–15. The number of passes resulted in seven complete loops with the tops of the loops engaged in the dermis. The tissues were held together only by the sutures.

Biomechanical strength testing was carried out as follows. Each sample was positioned so that the surface of the tissue sample was substantially vertical and the incision was generally horizontal. The bottom edge of the sample was immovably secured. The upper edge of the sample was attached to a Berkley digital fish scale (0–50 lb.) The scale was then raised vertically generating tension across the wound. The scale was raised until the tissues totally separated. The peak force required to separate the incision was recorded as the breaking strength.

TABLE 1

| Suture Method | Breaking Strength (lbs.) |
|---|---|
| Ruff Method | 4.5 |
| Buncke Method | 8.5 |
| Zigzag Method | 18.3 |
| Corkscrew Method | 16.5 |

EXAMPLE 2

Seven incisions were made at various locations on each of three dogs. The length of the incisions ranged from ½ inch to 4 inches and the depth of the incisions from the dermis to the muscular level. The incisions were closed with barbed sutures made from monofilament PDS (polydioxanone) size 0 and conventional sutures according to the following scheme with the locations randomized:

TABLE 2

| Tissue Level | Barbed Suture Method | Conventional Suture Method |
|---|---|---|
| Dermis | Alpha, Zigzag | Simple interrupted loop stitches [2-0 nylon, 2-0 silk] |
| Subcuticular | Corkscrew | Simple continuous loop stitches [3-0 PDS] |
| Subcutaneous | Corkscrew | Simple continuous loop stitches [3-0 PDS] |
| Muscular | Corkscrew | Simple continuous loop stitches [3-0 PDS] |

More than one alpha-shaped stitch was used for longer incisions.

The dogs were housed for two weeks. Daily clinical and necropsy observations were performed on all surgical sites. With the exception that three of six sites closed by nylon sutures had some sutures chewed out by the dog, all incisions healed normally and no dehiscence occurred. The other three sites closed with nylon sutures had a "railroad-tile" appearance, one site in particular being very pronounced. None of the topical skin sites closed with barbed sutures had such an appearance. This example shows the efficacy of barbed sutures in an in vivo model.

The methods of the present invention have a number of advantages, including improving the biomechanical performance of barbed sutures. The curvilinear placement paths of the suture, as contrasted with linear insertion, provide substantially increased strength for holding the edges of a wound together. Moreover, the insertion of a single suture with curvilinear techniques replaces the insertion of a plurality of sutures. The new methods provide an efficient means for a surgeon to close a wound, reducing the time necessary to place the suture and the trauma to the patient. Surgeons can quickly and easily utilize the suturing methods during any type of surgery to quickly join the edges of a wound in tissue without threading and tying numerous individual stitches. The new suture methods are performed in a manner similar to conventional suturing thus realizing the advantages thereof. The methods minimize damage to tissue when inserted and minimize scarring or tissue necrosis across the wound. The sutures can be placed in the tissue in a manner to control and adjust the tension on the suture or the compression of the tissue.

Although the present invention has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages of the invention, particularly in light of the foregoing teachings. For example, the methods of the present invention can be used alone or with other closure methods, such as topical skin adhesives to aid in holding the position of the tissue. Accordingly, we intend to cover all such modifications, omission, additions and equivalents as may be included within the spirit and scope of the invention as defined by the following claims.

We claim:

1. A method for joining and holding closed a wound in bodily tissue to allow tissue healing and regrowth together of sides or faces of the wound, or reconfiguration in vivo, using a barbed suture including an elongated body, first and second sharp pointed distal ends for penetrating the tissue, and a plurality of barbs extending from the periphery of the body, the barbs on a first portion of the body between the first end of the suture and a first axial location on the body for permitting movement of the suture through the tissue in a direction of movement of the first end and preventing movement of the suture relative to the tissue in a direction opposite the direction of movement of the first end, and the barbs on a second portion of the body between the second end of the suture and a second axial location on the body which is less than the distance from the second end to the first axial location permitting movement of the suture through the tissue in a direction of movement of the second end and preventing movement of the suture relative to the tissue in a direction opposite the direction of movement of the second end, the method comprising the steps of:

(a) inserting the first pointed end of the suture into the tissue at a first side of the wound;

(b) pushing the first end of the suture through the tissue until the first end of the suture extends out of the tissue at an exit point in the face of the wound below the surface of the tissue at the first side of the wound;

(c) gripping the first end of the suture and pulling the first end out of the tissue for drawing the first portion of the suture through the tissue until the second axial location is at the point of insertion of the first end of the suture and leaving a length of the first portion of the suture in the tissue between the point of insertion in the first side of the wound and the exit point in the face of the wound at the first side of the wound;

(d) inserting the first end of the suture into the face of the tissue below the surface of the tissue at a second side of the wound;

(e) pushing the first end of the suture through the tissue until the first end of the suture extends out of the tissue at an exit point on the second side of the wound longitudinally spaced in a first direction from the insertion point in the first side of the wound;

(f) gripping the first end of the suture and pulling the first end out of the tissue for drawing the first portion of the suture through the tissue while bringing the two sides of the wound together to a closed position along the first portion of the suture in the tissue and leaving a length of the first portion of the suture in the tissue between the point of insertion in the first side of the wound and the exit point in the second side of the wound;

(g) inserting the second pointed end of the suture into the tissue at one side of the wound;

(h) pushing the second end of the suture through the tissue until the second end of the suture extends out of the tissue at an exit point in the face of the tissue below the surface of the tissue at the one side of the wound;

(i) gripping the second end of the suture and pulling the second end out of the tissue for drawing the second portion of the suture through the tissue until the second axial location is at the point of insertion of the second end of the suture and leaving a length of the second portion of the suture in the tissue between the point of insertion in the one side of the wound and the exit point in the face of the wound at the one side of the wound;

(j) inserting the second end of the suture into the face of the tissue below the surface of the tissue at the other side of the wound;

(k) pushing the second end of the suture through the tissue until the second end of the suture extends out of the tissue at an exit point on the other side of the wound longitudinally spaced in a second direction from the point of insertion of the second end of the suture at the one side of the wound; and (l) gripping the second end of the suture and pulling the second end out of the tissue for drawing the second portion of the suture through the tissue while bringing the sides of the wound together to the closed position along the second portion of the suture in the tissue and leaving a length of the second portion of the suture in the tissue between the point of insertion in the one side of the wound and the exit point in the other side of the wound.

2. A method for joining and holding closed a wound in bodily tissue as recited in claim 1, wherein the point of insertion of the first pointed end of the suture is laterally spaced from the face of the wound at the first side of the wound.

3. A method for joining and holding closed a wound in bodily tissue as recited in claim 1, wherein the point of insertion of the first pointed end of the suture is into the face of the wound below the surface of the tissue at the first side of the wound.

4. A method for joining and holding closed a wound in bodily tissue as recited in claim 3, wherein the point of insertion of the first pointed end of the suture is adjacent an end of the wound.

5. A method for joining and holding closed a wound in bodily tissue as recited in claim 1, wherein the point of insertion of the first pointed end of the suture is longitudinally spaced from the ends of the wound.

6. A method for joining and holding closed a wound in bodily tissue as recited in claim 5, wherein the point of insertion of the first pointed end of the suture is laterally spaced from the face of the wound at the first side of the wound.

7. A method for joining and holding closed a wound in bodily tissue as recited in claim 5, wherein the point of insertion of the first pointed end of the suture is into the face of the wound below the surface of the tissue at the first side of the wound.

8. A method for joining and holding closed a wound in bodily tissue as recited in claim 1, wherein the steps of pushing the ends of the suture through the tissue comprise pushing the sutures along a curvilinear path.

9. A method for joining and holding closed a wound in bodily tissue as recited in claim 1, wherein the steps of pushing the ends of the suture through the tissue comprise pushing the ends along a straight path.

10. A method for joining and holding closed a wound in bodily tissue as recited in claim 1, wherein the first end of the suture exits from the face of the wound below the surface of the tissue on the second side of the wound.

11. A method for joining and holding closed a wound in bodily tissue as recited in claim 1, wherein the first end of the suture exits the second side of the wound at a point laterally spaced from the face on the second side of the wound.

12. A method for joining and holding closed an open wound in bodily tissue as recited in claim 1, wherein the step of inserting the second pointed end of the suture is at the point of insertion of the first pointed end laterally spaced from a first side of the wound.

13. A method for joining and holding closed an open wound in bodily tissue as recited in claim 1, wherein the step of inserting the second pointed end of the suture is into the tissue of the second face of the wound below the surface of the tissue.

14. A method for joining and holding closed an open wound in bodily tissue as recited in claim 1, wherein the paths of the first and second portions of the suture overlap below the surface of the tissue.

15. A method for joining and holding closed a wound in bodily tissue to allow tissue healing and regrowth together of sides or faces of the wound, or reconfiguration in vivo, the method comprising the steps of:

(a) providing a barbed suture including an elongated body, first and second sharp pointed distal ends for penetrating the tissue, and a plurality of barbs extending from the periphery of the body, the barbs on a first portion of the body between the first end of the suture and a first axial location on the body for permitting movement of the suture through the tissue in a direction of movement of the first end and preventing movement of the suture relative to the tissue in a direction opposite the direction of movement of the first end, and the barbs on a second portion of the body between the second end of the suture and a second axial location on the body which is less than the distance from the second end to the first axial location permitting movement of the suture through the tissue in a direction of movement of the second end and preventing movement of the suture relative to the tissue in a direction opposite the direction of movement of the second end;

(b) inserting the first pointed end of the suture into the tissue at a first side of the wound;

(c) pushing the first end of the suture through the tissue until the first end of the suture extends out of the tissue at an exit point in the face of the wound below the surface of the tissue at the first side of the wound;

(d) gripping the first end of the suture and pulling the first end out of the tissue for drawing the first portion of the suture through the tissue until the second axial location is at the point of insertion of the first end of the suture and leaving a length of the first portion of the suture in the tissue between the point of insertion in the first side of the wound and the exit point in the face of the wound at the first side of the wound;

(e) inserting the first end of the suture into the face of the tissue below the surface of the tissue at a second side of the wound;

(f) pushing the first end of the suture through the tissue until the first end of the suture extends out of the tissue at an exit point on the second side of the wound longitudinally spaced in a first direction from the insertion point in the first side of the wound;

(g) gripping the first end of the suture and pulling the first end out of the tissue for drawing the first portion of the suture through the tissue while bringing the two sides of the wound together to a closed position along the first portion of the suture in the tissue and leaving a length of the first portion of the suture in the tissue between the point of insertion in the first side of the wound and the exit point in the second side of the wound;

(h) inserting the second pointed end of the suture into the tissue at one side of the wound;

(i) pushing the second end of the suture through the tissue until the second end of the suture extends out of the tissue at an exit point in the face of the tissue below the surface of the tissue at the one side of the wound;

(j) gripping the second end of the suture and pulling the second end out of the tissue for drawing the second portion of the suture through the tissue until the second axial location is at the point of insertion of the second end of the suture and leaving a length of the second portion of the suture in the tissue between the point of insertion in the one side of the wound and the exit point in the face of the wound at the one side of the wound;

(k) inserting the second end of the suture into the face of the tissue below the surface of the tissue at the other side of the wound;

(l) pushing the second end of the suture through the tissue until the second end of the suture extends out of the tissue at an exit point on the other side of the wound longitudinally spaced in a second direction from the point of insertion of the second end of the suture at the one side of the wound; and (m) gripping the second end of the suture and pulling the second end out of the tissue for drawing the second portion of the suture through the tissue while bringing the sides of the wound together to the closed position along the second portion of the suture in the tissue and leaving a length of the second portion of the suture in the tissue between the point of insertion in the one side of the wound and the exit point in the other side of the wound.

16. A method for joining and holding closed an open wound in bodily tissue as recited in claim 15, wherein the first and second sharp pointed distal ends are straight.

17. A method for joining and holding closed an open wound in bodily tissue as recited in claim 15, wherein the first and second sharp pointed distal ends are curved.

18. A method for joining and holding closed an open wound in bodily tissue as recited in claim 15, wherein the first and second sharp pointed distal ends are surgical needles.

19. A method for joining and holding closed an open wound in bodily tissue as recited in claim 18, wherein the needles are straight.

20. A method for joining and holding closed an open wound in bodily tissue as recited in claim 18, wherein the needles are curved.

21. A method for joining and holding closed a wound in bodily tissue to allow tissue healing and regrowth together of the sides of the wound, or reconfiguration in vivo, using a barbed suture including an elongated body, first and second sharp pointed distal ends for penetrating the tissue, and a plurality of barbs extending from the periphery of the body, the barbs on a first portion of the body between the first end of the suture and a first axial location on the body for permitting movement of the suture through the tissue in a direction of movement of the first end and preventing movement of the suture relative to the tissue in a direction opposite the direction of movement of the first end, and the barbs on a second portion of the body between the second end of the suture and a second axial location on the body which is less than the distance from the second end to the first axial location permitting movement of the suture through the tissue in a direction of movement of the second end and preventing movement of the suture relative to the tissue in a direction opposite the direction of movement of the second end, the method comprising the steps of:

(a) inserting the first pointed end of the suture into the tissue at a point laterally spaced from a face of the wound at one side of the wound;

(b) pushing the first end of the suture through the tissue until the first end of the suture extends out of the tissue at an exit point in the face of the wound below the surface of the tissue at the one side of the wound and penetrating the tissue of a face of the wound below the surface of the tissue at another side of the wound until the first end of the suture extends out of the tissue at an exit point laterally spaced from the face on the other side of the wound and longitudinally spaced in a first direction from the point of insertion of the first end of the suture at the one side of the wound;

(c) gripping the first pointed end of the suture and pulling the first end out of the tissue for drawing the first portion of the suture through the tissue while bringing the two sides of the tissue together to a closed position along the first portion of the suture until the second axial location is at the point of insertion of the first end of the suture at the one side of the wound and leaving a length of the first portion of the suture in the tissue between the point of insertion and the exit point;

(d) inserting the second end of the suture into the tissue at the insertion point of the first end;

(e) pushing the second end of the suture through the tissue until the second end of the suture extends out of the tissue at an exit point in the face of the wound below the surface of the tissue at the one side of the wound and penetrating the tissue of a face of the wound below the surface of the tissue at another side of the wound until the second end of the suture extends out of the tissue at an exit point laterally spaced from the face on the other side of the wound and longitudinally spaced in the second direction from the point of insertion of the second end of the suture at the one side of the wound; and (f) gripping the second end of the suture and pulling the second end out of the tissue for drawing the second portion of the suture through the tissue while bringing the two sides of the tissue together to the closed position along the second portion of the suture and leaving a length of the second portion of the suture in the tissue between the point of insertion and the exit point.

22. A method for joining and holding closed a wound in bodily tissue as recited in claim 21, further comprising the steps of:

(a) inserting the first end of the suture into the tissue at the exit point of the first end;

(b) pushing the first end of the suture through the tissue until the first end of the suture extends out of the tissue at an exit point in the face of the wound below the surface of the tissue at the side of the wound and penetrating the tissue of a face of the wound below the surface of the tissue at another side of the wound until the first end of the suture extends out of the tissue at an exit point laterally spaced from the face on the other side of the wound and longitudinally spaced in the first direction from the immediately preceding point of insertion of the first end of the suture at the side of the wound;

(c) gripping the first pointed end of the suture and pulling the first end out of the tissue for drawing the first portion of the suture through the tissue while bringing the two sides of the tissue together to a closed position along the first portion of the suture and leaving a length of the first portion of the suture in the tissue between the point of insertion and the exit point;

(d) repeating steps (a) through (c) for advancing longitudinally along the wound in the first direction to one end of the wound;

(e) inserting the second pointed end of the suture into the tissue at the exit point of the second end at the side of the wound;

(f) pushing the second end of the suture through the tissue until the second end of the suture extends out of the tissue at an exit point in the face of the wound below the surface of the tissue at the side of the wound and penetrating the tissue of a face of the wound below the surface of the tissue at another side of the wound until the second end of the suture extends out of the tissue at an exit point laterally spaced from the face on the other side of the wound and longitudinally spaced in a second direction from the point of insertion of the second end of the suture at the one side of the wound;

(g) gripping the second pointed end of the suture and pulling the second end out of the tissue for drawing the second portion of the suture through the tissue while bringing the two sides of the tissue together to a closed position along the second portion of the suture until the second axial location is at the point of insertion of the first end of the suture at the one side of the wound and leaving a length of the second portion of the suture in the tissue between the point of insertion and the exit point; and (h) repeating steps (e) through (g) for advancing longitudinally along the wound in the second direction to the other end of the wound.

23. A method for joining and holding closed a wound in bodily tissue as recited in claim 21, wherein the steps of pushing the ends of the suture through the tissue comprise pushing the ends along curvilinear paths and the the paths of the first and second portions of the suture in the other side of the wound overlap below the surface of the tissue.

24. A method for joining and holding closed a wound in bodily tissue to allow tissue healing and regrowth together of the sides of the wound, or reconfiguration in vivo, using a barbed suture including an elongated body, first and second sharp pointed distal ends for penetrating the tissue, and a plurality of barbs extending from the periphery of the body, the barbs on a first portion of the body between the first end of the suture and a first axial location on the body for permitting movement of the suture through the tissue in a direction of movement of the first end and preventing movement of the suture relative to the tissue in a direction opposite the direction of movement of the first end, and the barbs on a second portion of the body between the second end of the suture and a second axial location on the body which is less than the distance from the second end to the first axial location permitting movement of the suture through the tissue in a direction of movement of the second end and preventing movement of the suture relative to the tissue in a direction opposite the direction of movement of the second end, the method comprising the steps of:

(a) inserting the first pointed end of the suture into the tissue below the surface of the tissue at a first face of the wound at an initial point longitudinally spaced from the ends of the wound;

(b) pushing the first end of the suture through the tissue along a curvilinear path until the first end of the suture extends from the tissue at a subcutaneous exit point in the first face of the wound longitudinally spaced in a first direction from the insertion point in the first face of the wound;

(c) gripping the first pointed end of the suture and pulling the first end out of the tissue for drawing the first portion of the suture through the tissue until the second axial location is at the point of insertion of the first end of the suture in the first face of the wound and leaving a length of the first portion of the suture in the tissue of the wound;

(d) inserting the first pointed end of the suture at a point below the surface of the tissue in a second face of the wound;

(e) pushing the first end of the suture through the tissue along a curvilinear path until the first end of the suture extends from the tissue at an exit point in the second face of the wound below the surface of the tissue and longitudinally spaced in the first direction from the insertion point in the second face of the wound;

(f) inserting the first end of the suture at a point in the first face of the wound below the surface of the tissue;

(g) repeating steps (b) through (f) for advancing longitudinally along the wound in the first direction as necessary to one end of the wound;

(h) inserting the second pointed end of the suture into the tissue of the second face of the wound below the surface of the tissue and adjacent the initial point of insertion of the first end in the first face of the wound;

(i) pushing the second end of the suture through the tissue along a curvilinear path until the second end of the suture extends from the tissue at an exit point below the surface of the tissue in the second face of the wound and longitudinally spaced in a second direction from the point of insertion in the second face of the wound;

(j) gripping the second pointed end of the suture and pulling the second end out of the tissue for drawing the second portion of the suture through the tissue until the second axial location is at the point of insertion of the second needle in the second face of the wound and leaving a length of the second portion of the suture in the tissue of the wound;

(k) inserting the second pointed end of the suture at a point in the first face of the wound below the surface of the tissue;

(l) pushing the second end of the suture through the tissue along a curvilinear path until the second end of the suture extends from the tissue at an exit point in the first face of the wound below the surface of the tissue and longitudinally spaced in the second direction from the point of insertion of the second end of the suture in the first face of the wound;

(m) inserting the second pointed end of the suture at a point in the first face of the wound below the surface of the tissue; and (n) repeating steps (i) through (m) for advancing longitudinally along the wound in the second direction to the other end of the wound.

25. A method for joining and holding closed a wound in bodily tissue to allow tissue healing and regrowth together of the sides of the wound, or reconfiguration in vivo, using a barbed suture including an elongated body, first and second sharp pointed distal ends for penetrating the tissue, and a plurality of barbs extending from the periphery of the body, the barbs on a first portion of the body between the first end of the suture and a first axial location on the body for permitting movement of the suture through the tissue in a direction of movement of the first end and preventing movement of the suture relative to the tissue in a direction opposite the direction of movement of the first end, and the barbs on a second portion of the body between the second end of the suture and a second axial location on the body which is less than the distance from the second end to the first axial location permitting movement of the suture through the tissue in a direction of movement of the second end and preventing movement of the suture relative to the tissue in a direction opposite the direction of movement of the second end, the method comprising the steps of:

(a) inserting the first pointed end of the suture into the tissue below the surface of the tissue of a first face of the wound at an initial point adjacent an end of the wound;

(b) pushing the first end of the suture through the tissue along a curvilinear path until the first end of the suture extends from the tissue at an exit point in the first face of the wound below the surface of the tissue and longitudinally spaced from the end of the wound in a direction toward the other end of the wound;

(c) gripping the first pointed end of the suture and pulling the first end out of the tissue for drawing the first portion of the suture through the tissue until the second axial location is at the point of insertion of the first end of the suture in the first face of the wound and leaving a length of the first portion of the suture in the tissue of the wound;

(d) inserting the first end of the suture into the second face of the wound below the surface of the tissue;

(e) pushing the first end of the suture through the tissue along a curvilinear path until the first end extends from the tissue at an exit point in the second face of the wound below the surface of the tissue and longitudinally spaced from the insertion point in the second face of the wound toward the other end of the wound;

(f) inserting the first end of the suture into the first face of the wound below the surface of the tissue;

(g) repeating steps (b) through (f) for advancing longitudinally along the wound in the direction toward the other end of the wound until the other end of the wound is reached;

(h) inserting the second pointed end of the suture into the tissue of the second face of the wound below the surface of the tissue adjacent the initial point of insertion of the first pointed end of the suture;

(i) pushing the second end of the suture through the tissue along a curvilinear path until the second end extends from the tissue at an exit point in the second face of the wound below the surface of the tissue and longitudinally spaced from the one end of the wound in a direction toward the other end of the wound;

(j) gripping the second end of the suture and pulling the second end out of the tissue for drawing the second portion of the suture through the tissue until the second axial location is at the point of insertion of the second end of the suture in the first face of the wound and leaving a length of the second portion of the suture in the tissue of the open wound;

(k) inserting the second end of the suture into the first face of wound below the surface of the tissue adjacent the exit point of the first end of the suture;

(l) pushing the second end of the suture through the tissue along a curvilinear path until the second end of the suture extends from the tissue at an exit point in the first face of the wound below the surface of the tissue and longitudinally spaced from the exit point in the first face of the wound in a direction toward the other end of the wound;

(m) inserting the second end of the suture into the second face of the wound below the surface of the tissue; and (n) repeating steps (i) through (m) for advancing longitudinally along the wound in the direction toward the other end of the wound until the other end of the wound is reached.

26. A method for joining two ends of severed internal tissue to allow tissue healing and regrowth together of the two ends of the internal tissue in vivo using a barbed suture including an elongated body, first and second sharp pointed distal ends for penetrating the tissue, and a plurality of barbs extending from the periphery of the body, the barbs on a first portion of the body between the first end of the suture and a first axial location on the body for permitting movement of the suture through the tissue in a direction of movement of the first end and preventing movement of the suture relative to the tissue in a direction opposite the direction of movement of the first end, and the barbs on a second portion of the body between the second end of the suture and a second axial location on the body which is less than the distance from the second end to the first axial location permitting movement of the suture through the tissue in a direction of movement of the second end and preventing movement of the suture relative to the tissue in a direction opposite the direction of movement of the second end, the method comprising the steps of:

(a) inserting the first pointed end of the suture into a first end of the internal tissue;

(b) pushing the first end of the suture through the internal tissue along a curvilinear path until the point at the first end of the suture extends from an exit point in the periphery of the internal tissue longitudinally spaced from the first end of the internal tissue;

(c) gripping the first pointed end of the suture and pulling the first end out of the internal tissue for drawing the first portion of the suture through the internal tissue until the first axial location is adjacent the end of the internal tissue for leaving a length of the first portion of the suture in the internal tissue;

(d) inserting the first end of the suture into the periphery of the internal tissue adjacent the exit point;

(e) pushing the first end of the suture along a curvilinear path until the point at the first end of the suture extends from an exit point in the periphery of the internal tissue opposite and longitudinally spaced from the previous insertion point in the periphery of the internal tissue; and (f) repeating steps (a) through (e) with the second pointed end of the suture at the other end of the internal tissue.

27. A method for joining two ends of severed internal tissue as recited in claim 26, further comprising the steps of:

(a) inserting the first pointed end of a second suture into the one end of the internal tissue;

(b) pushing the first end of the suture through the internal tissue along a curvilinear path until the point at the first end of the suture extends from an exit point in the periphery of the internal tissue longitudinally spaced from the one end of the internal tissue and substantially opposite the initial exit point of the first suture;

(c) gripping the first pointed end of the second suture and pulling the first end out of the internal tissue for drawing the first portion of the suture through the internal tissue until the first axial location is adjacent the end of the internal tissue and leaving a length of the first portion of the suture in the internal tissue;

(d) inserting the first end of the second suture into the periphery of the internal tissue adjacent the exit point;

(e) pushing the first end of the second suture along a curvilinear path until the point at the first end extends from an exit point in the periphery of the internal tissue longitudinally spaced from the insertion point in the second side of the internal tissue; and (f) repeating steps (a) through (e) with the second end of the second suture at the other end of the internal tissue.

\* \* \* \* \*